United States Patent
Walden, II et al.

(10) Patent No.: US 12,130,858 B2
(45) Date of Patent: *Oct. 29, 2024

(54) SYSTEMS AND METHODS OF METADATA AND IMAGE MANAGEMENT FOR REVIEWING DATA FROM TRANSMISSION ELECTRON MICROSCOPE (TEM) SESSIONS

(71) Applicant: Protochips, Inc., Morrisville, NC (US)

(72) Inventors: Franklin Stampley Walden, II, Raleigh, NC (US); John Damiano, Jr., Holly Springs, NC (US); David P. Nackashi, Raleigh, NC (US); Daniel Stephen Gardiner, Wake Forest, NC (US); Mark Uebel, Morrisville, NC (US); Alan Philip Franks, Durham, NC (US); Joshua Friend, Raleigh, NC (US); Katherine Elizabeth Marusak, Cary, NC (US)

(73) Assignee: Protochips, Inc., Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/244,587

(22) Filed: Sep. 11, 2023

(65) Prior Publication Data

US 2023/0418863 A1     Dec. 28, 2023

Related U.S. Application Data

(63) Continuation of application No. 17/931,466, filed on Sep. 12, 2022, now Pat. No. 11,755,639, which is a
(Continued)

(51) Int. Cl.
*A61B 6/00*   (2024.01)
*G06F 16/51*   (2019.01)
(Continued)

(52) U.S. Cl.
CPC ............ *G06F 16/535* (2019.01); *G06F 16/51* (2019.01); *G06F 16/538* (2019.01);
(Continued)

(58) Field of Classification Search
CPC ...... G06F 16/535; G06F 16/51; G06F 16/538; G06F 16/5866; G06T 1/0007; G06T 7/20;
(Continued)

(56) References Cited

U.S. PATENT DOCUMENTS 6,512,842 B1 *  1/2003  Steffan ................ G06V 10/987
                                                        382/149
8,933,401 B1    1/2015  Reed
(Continued)

FOREIGN PATENT DOCUMENTS

WO   2006125188 A1   11/2006
WO   2021034569 A2   2/2021

OTHER PUBLICATIONS

ISA/US; International Search Report and Written Opinion for International Patent Application No. PCT/US2022/023892 dated Aug. 10, 2022, 13 pages.
(Continued)

*Primary Examiner* — Howard D Brown, Jr.
(74) *Attorney, Agent, or Firm* — NK Patent Law

(57) ABSTRACT

Disclosed herein are methods and systems of metadata management for reviewing data from microscopy experimental sessions. Image data from an experimental session is stored in an archive at one or more filepath locations, either locally or on a network. Metadata associated with the image data is stored in a database with a reference to the filepath where the raw image is stored, such that the metadata is associated in the database with the image data. A user can perform post-experimental filtering, sorting, and searching of the underlying image data using the metadata, which
(Continued)

allows the image data to be analyzed without duplication of the image data and without manual review of each individual image. The filtered data is presented in an interactive timeline format.

20 Claims, 20 Drawing Sheets

Related U.S. Application Data continuation of application No. 17/715,831, filed on Apr. 7, 2022, now Pat. No. 11,455,333, which is a continuation of application No. PCT/US2022/023892, filed on Apr. 7, 2022.

(60) Provisional application No. 63/171,692, filed on Apr. 7, 2021.

(51) Int. Cl.
 G06F 16/535 (2019.01)
 G06F 16/538 (2019.01)
 G06F 16/58 (2019.01)
 G06T 1/00 (2006.01)
 G06T 7/20 (2017.01)
 G06T 11/60 (2006.01)

(52) U.S. Cl.
 CPC ........ *G06F 16/5866* (2019.01); *G06T 1/0007* (2013.01); *G06T 7/20* (2013.01); *G06T 11/60* (2013.01); *G06T 2200/24* (2013.01); *G06T 2207/10061* (2013.01)

(58) Field of Classification Search
 CPC .................. G06T 11/60; G06T 2200/24; G06T 2207/10061
 See application file for complete search history.

(56) References Cited

U.S. PATENT DOCUMENTS

| | | | |
|---|---|---|---|
| 10,990,797 B2* | 4/2021 | Cotte | G06V 20/698 |
| 2002/0124018 A1 | 9/2002 | Fifield et al. | |
| 2007/0023651 A1 | 2/2007 | Ishitani et al. | |
| 2008/0073533 A1 | 3/2008 | Makino et al. | |
| 2010/0116977 A1 | 5/2010 | Young et al. | |
| 2013/0146784 A1 | 6/2013 | Nackashi et al. | |
| 2014/0226003 A1 | 8/2014 | Phaneuf et al. | |
| 2014/0380531 A1 | 12/2014 | Ukraintsev et al. | |
| 2015/0016727 A1 | 1/2015 | Latin-Stoermer et al. | |
| 2015/0227518 A1 | 8/2015 | Kallan | |
| 2016/0064187 A1 | 3/2016 | Tomimatsu et al. | |
| 2016/0172154 A1 | 6/2016 | Kakinuma et al. | |
| 2018/0039054 A1 | 2/2018 | Hattori | |
| 2018/0204704 A1 | 7/2018 | Suzuki et al. | |
| 2018/0204705 A1 | 7/2018 | Tomimatsu et al. | |
| 2019/0017811 A1 | 1/2019 | Watanabe et al. | |
| 2019/0304745 A1 | 10/2019 | Suzuki et al. | |
| 2021/0200884 A1* | 7/2021 | Anand | G06F 21/566 |
| 2021/0235021 A1* | 7/2021 | Walden, II | G06T 7/337 |
| 2021/0321963 A1* | 10/2021 | Manor | G16H 50/20 |
| 2021/0381992 A1 | 12/2021 | Aguiar | |
| 2023/0049691 A1* | 2/2023 | Walden, II | G06F 16/51 |

OTHER PUBLICATIONS

Clare et al. "Electron Bio-Imaging Centre (eBIC): the UK national research facility for biological electron microscopy." Acta Crystallographica Section D: Structural Biology 73.6 (2017): 488-495. May 24, 2017 (May 24, 2017) Retrieved on Jul. 16, 2022 (Jul. 16, 2022) from <https:/fscripts.iucr.org/cgi-bin/paper?ic5100> entire document.

USPTO, Non-Final Office Action for corresponding U.S. Appl. No. 17/931,466, mailed Jan. 12, 2023, 8 pages.

"Search and find photos". Adobe. Dec. 13, 2017. https://helpx.adobe.com/lightroom-cc/how-to/search-find-photos-ratings-flags-lightroom-cc.html.

"Velox". Thermo Fisher Scientific. https://www.thermofisher.com/order/catalog/product/VELOX.

"DigitalMicrograph Software". Gatan Ametek. https://www.gatan.com/products/tem-analysis/gatan-microscopy-suite-software.

"Security & Stock Screeners". Fidelity. https://research2.fidelity.com/fidelity/screeners/commonstock/landing.asp.

"Use filtering to modify a SharePoint view". Microsoft. https://support.microsoft.com/en-us/office/use-filtering-to-modify-a-sharepoint-view-3d8efc52-0808-4731-8f9b-3dfaeacea3d4.

* cited by examiner

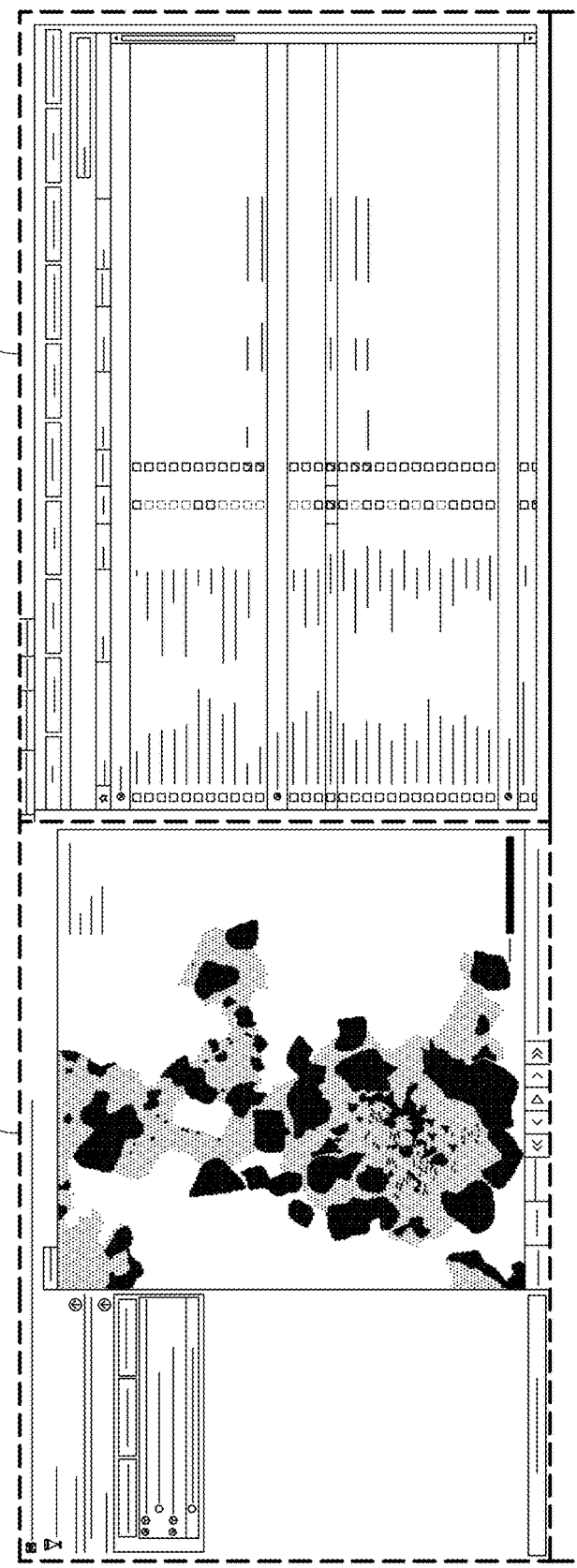
FIG. 9
FIG. 7
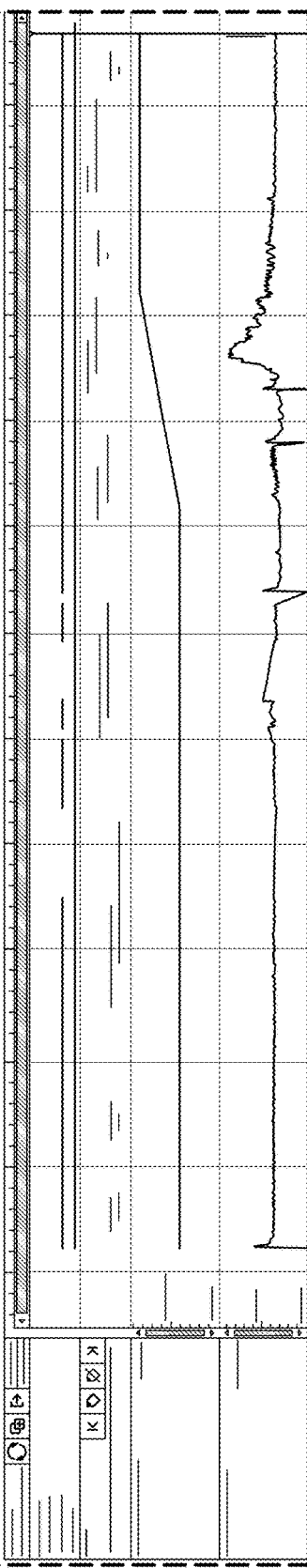
FIG. 5
FIG. 4

| | | | | | | | | | |
|---|---|---|---|---|---|---|---|---|---|
| Image Metadata | Favorites | AXON | Image Analysis | Dose | Microscope | Service | Position | Toolbox | Drift Correction | Focus Assist | Image | Atmosphere 210 |

Search

| ☆ | Name | Value | Units | Plot | Overlay | Title | Location | Size(pt) | Font |
|---|---|---|---|---|---|---|---|---|---|
| ⓘ | AXON | | | | | | | | |
| ☐ | File Size | 0 | | ☐ | | | | | |
| ☐ | Image Source | Synchronicity | | | | | | | |
| ☐ | Session Name | 2021-04-26-222239-Atm... | | ☐ | | | | | |
| ☐ | AXON Version | 10.4.4.21 | | ☐ | | | | | |
| ☐ | Local Date/Time | 04/26/2021 23:34:59.032 | | ☐ | | | | | |
| ☐ | Acquisition Image Number | 607 | | | ☐ | | | | |
| ☐ | Session Image Number | 607 | | | ☐ | | | | |
| ☐ | Imaging Date/Time | 04/27/2021 12:38:47.0000 | | ☐ | | | | | |
| ☐ | Microscope Date/Time | 04/26/2021 23:41:51.196 | | ☐ | | | | | |
| ☐ | Tags | "Running Focus Calibrati..." | | ☒ | | Tags | Top Left | 28 | Microsoft Sans Serif |
| ☐ | Scale Bar | | | ☒ | | | Bottom Right | 24 | Microsoft Sans Serif |
| ⓘ | Atmosphere210 | | | | | | | | |
| ☐ | Experiment Type | Flow | | ☐ | | | | | |
| ☐ | Experiment Log File | April-26-2021_1 | | ☐ | | | | | |
| ☐ | Experiment Elapsed Time | 0:03:33:37.274 | | ☐ | | | | | |
| ☒ | Holder Temperature | 250.0 | °C | ☒ | | | Top Left | 28 | Microsoft Sans Serif |
| ☐ | Holder Pressure | 700.3 | Torr | ☐ | | | | | |

FIG. 9A

| | | | | | |
|---|---|---|---|---|---|
| ☐ Holder Pressure | 700.3 | Torr | ☐ | | |
| ☐ Holder Gas | 10%H2-Ar(100%) | | ☒ | Top Left | 28 | Microsoft Sans Serif |
| ☐ Holder Flow Rate | 2.641E-07 | sccm | ☒ | Flow Rate Top Left | 28 | Microsoft Sans Serif |
| ☐ Tank 1 Pressure | 700.3 | Torr | ☐ | | |
| ☐ Tank 1 Gas | 10%H2-Ar(100%) | | ☐ | | |
| ☐ Tank 2 Pressure | 2.500 | Torr | ☐ | | |
| ☐ Tank 2 Gas | Vaccum | | ☐ | | |
| ☐ Vacuum Tank Pressure | 1.133 | Torr | ☐ | | |
| ☐ Vacuum Tank Gas | 10%H2-Ar(100%) | | ☐ | | |
| ☐ Heating Current | 0.002433 | A | ☐ | | |
| ☐ Heating Resistance | 7715 | Ω | ☐ | | |
| ☐ Heating Voltage | 18.77 | V | ☐ | | |
| ☐ Heating Power | 0.04566 | W | ☐ | | |
| ⊙ Drift correction | | | | | |
| ☐ Drift Corrcted image Number | 347 | | ☐ | | |

FIG. 9B

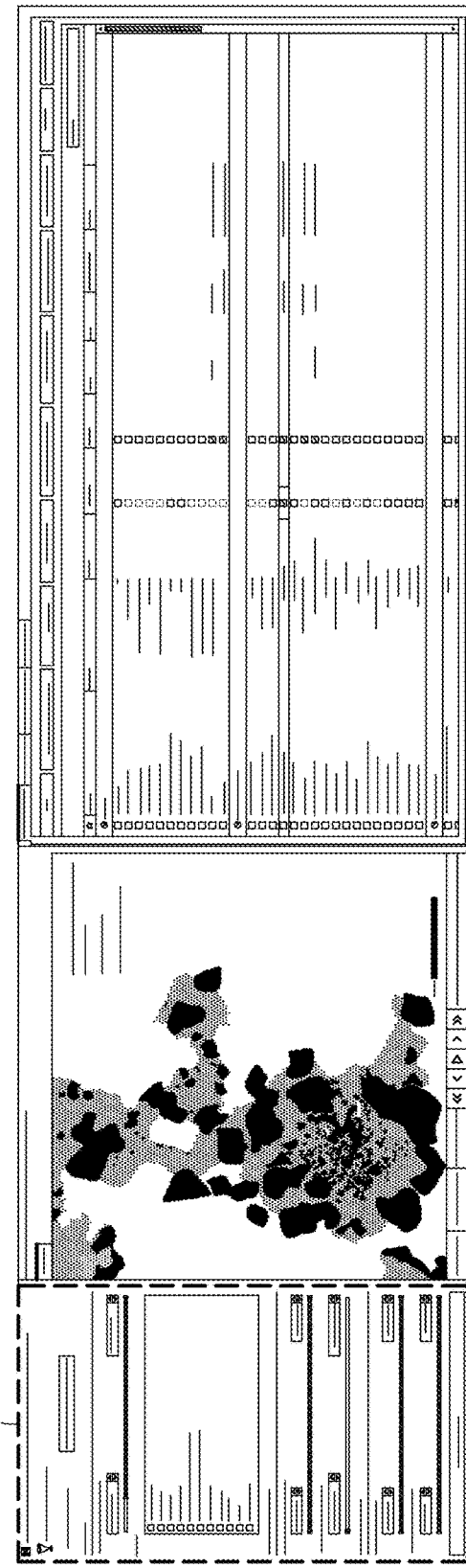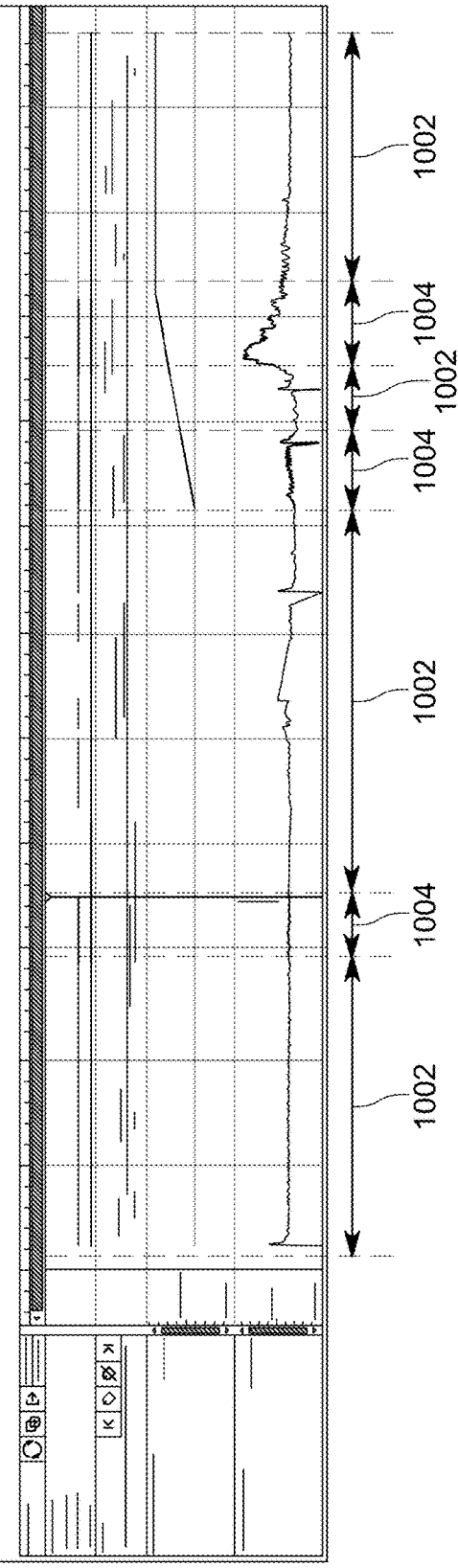
FIG. 10
FIG. 11

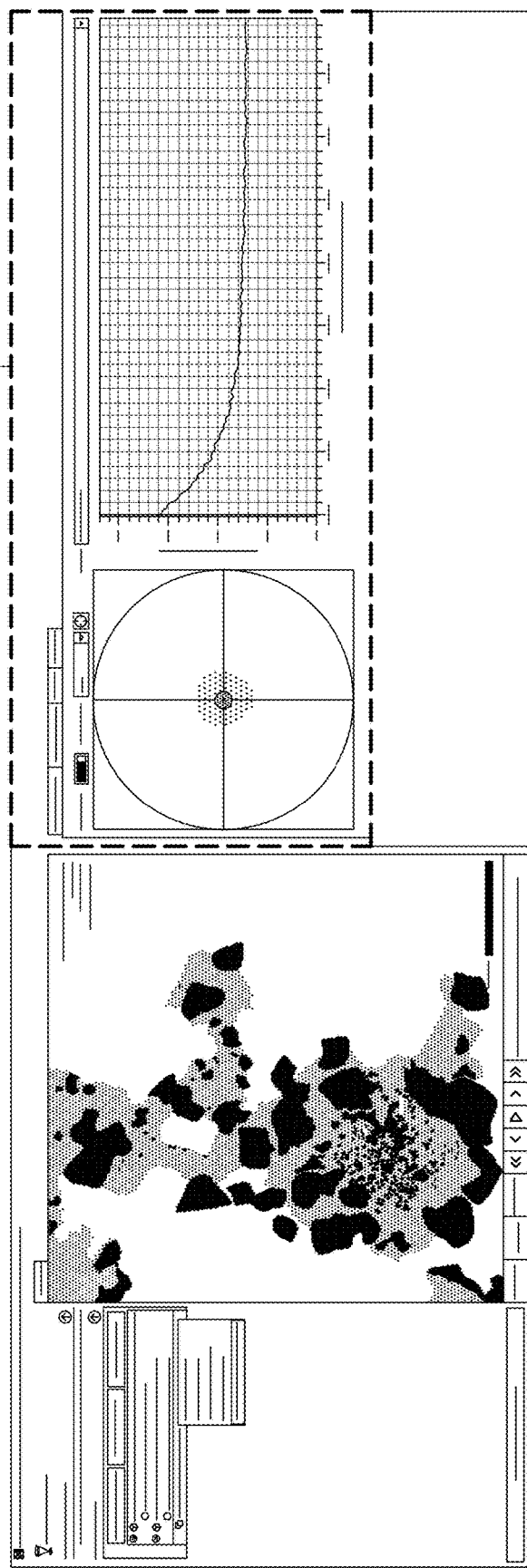
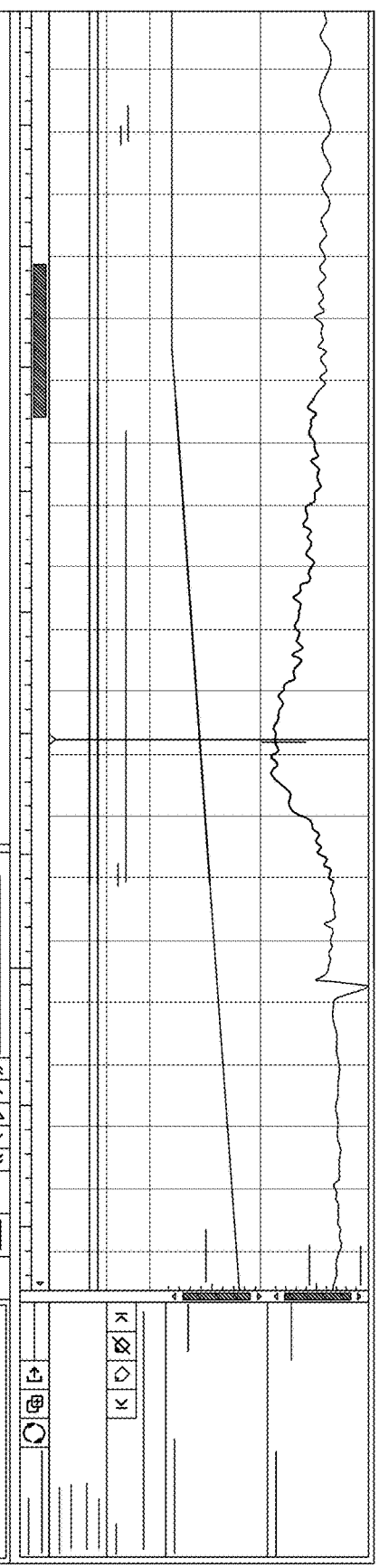
FIG. 13
FIG. 12

SYSTEMS AND METHODS OF METADATA AND IMAGE MANAGEMENT FOR REVIEWING DATA FROM TRANSMISSION ELECTRON MICROSCOPE (TEM) SESSIONS

CROSS-REFERENCE TO RELATED APPLICATIONS

This application is a continuation of U.S. Non-Provisional patent application Ser. No. 17/931,466 filed on Sep. 12, 2022 by Protochips, Inc. entitled "SYSTEMS AND METHODS OF METADATA AND IMAGE MANAGEMENT FOR REVIEWING DATA FROM TRANSMISSION ELECTRON MICROSCOPE (TEM) SESSIONS", issuing as U.S. Pat. No. 11,755,639 on Sep. 12, 2023, which is a continuation of U.S. Non-Provisional patent application Ser. No. 17/715,831 filed on Apr. 7, 2022 by Protochips, Inc. entitled "SYSTEMS AND METHODS OF METADATA AND IMAGE MANAGEMENT FOR REVIEWING DATA FROM TRANSMISSION ELECTRON MICROSCOPE (TEM) SESSIONS", now U.S. Pat. No. 11,455,333 issued on Sep. 27, 2022, which is a continuation of International Application No. PCT/US22/23892 filed on Apr. 7, 2022 by Protochips, Inc. entitled "SYSTEMS AND METHODS OF METADATA AND IMAGE MANAGEMENT FOR REVIEWING DATA FROM TRANSMISSION ELECTRON MICROSCOPE (TEM) SESSIONS," which claims priority to U.S. Provisional Patent Application No. 63/171,692 filed on Apr. 7, 2021 by Protochips, Inc. entitled "SYSTEMS AND METHODS OF METADATA AND IMAGE MANAGEMENT FOR REVIEWING DATA FROM TRANSMISSION ELECTRON MICROSCOPE (TEM) SESSIONS," the entire contents of all of which are incorporated by reference herein.

TECHNICAL FIELD

The present disclosure relates to the field of electron microscopy, and particularly to systems and methods of image and metadata management for reviewing data from TEM sessions.

BACKGROUND

In in situ microscopy, a transmission electron microscope (TEM) or scanning transmission electron microscope (STEM) uses a beam of electrons transmitted through a specimen in a sample holder to form an image. The TEM or STEM is used during experiments or experimental sessions to observe the sample over a period of time. One burden in the field of in situ microscopy, and generally all TEM microscopy, is the total amount of data accumulated both during a session and over the course of time. A single TEM session may span eight or more hours and may generate over one million images and over 800 GB of data. It is not unusual for a user to collect thousands or more of 16 MP images in a single session, which may total many terabytes of data. Additionally, users may accumulate many sessions on a single sample type across many TEMs. Modern cameras can collect coherent images at frame rates exceeding 40 frames/second at the maximum resolution, with trends toward an order of magnitude faster within the next five years. Thus, the volume of data generated from experimental sessions is large and unwieldy to analyze. Post-experiment analysis of such a large amount of data can be tedious, time-consuming, and resource-intensive.

Very few tools exist that allow a user to search, sort, and identify the most important sections of the data. This results in important scientific findings being buried in a sea of information, as well as leading to false conclusions that send research in the wrong direction. Thus, opportunities exist for providing a novel approach for post-experiment analysis of images to find and prepare critical images and sequences.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

The methods and systems of metadata management for a transmission electron microscope (TEM) described herein use experimental metadata, TEM metadata, and camera metadata from current and past experimental sessions taken from one or more different TEMs to provide users to a novel way to analyze and visualize the image stack in an efficient manner. This allows for post-experiment analysis that is used to find and prepare critical images and sequences from vast session data.

BRIEF DESCRIPTION OF THE FIGURES

FIG. 4 depicts a user-interface screen showing an Overview Panel of the metadata management system described herein.

FIGS. 9A-9B depict a detailed view of the Image Metadata Panel of the Overview panel of the metadata management system described herein.

FIG. 10 depicts a filtered view of the Overview Panel shown in FIG. 4.

FIG. 12 depicts the Overview Panel of FIG. 4 with the FFT Analysis Panel enabled in place of the Image Metadata Panel.

DETAILED DESCRIPTION

Figure 1:
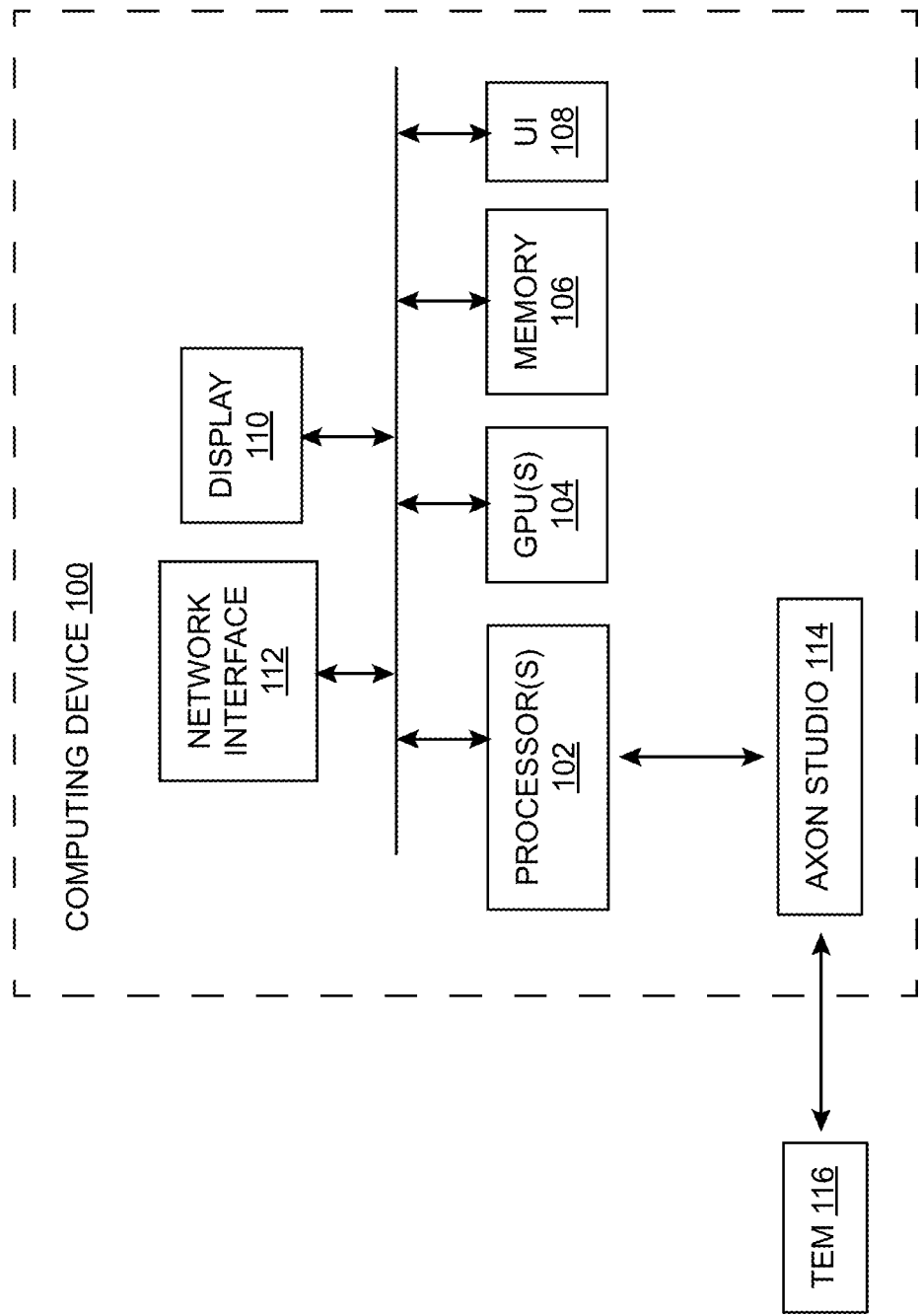
FIG. 1 depicts one embodiment of the system of metadata management for a transmission electron microscope described herein.

Below, the technical solutions in the examples of the present disclosure are depicted clearly and comprehensively with reference to the figures according to the examples of the present disclosure. Obviously, the examples depicted here are merely some examples, but not all examples of the present disclosure. In general, the components in the examples of the present disclosure depicted and shown in the figures herein can be arranged and designed according to different configurations. Thus, detailed description of the examples of the present disclosure provided in the figures below are not intended to limit the scope of the present disclosure as claimed, but merely represent selected examples of the present disclosure. On the basis of the examples of the present disclosure, all of other examples that could be obtained by a person skilled in the art without using inventive efforts will fall within the scope of protection of the present disclosure. The present disclosure will now we described with reference to the Figures shown below.

The systems and methods of metadata management for TEM described herein improves the functioning of a computer by providing an underlying data management system for data generated during an experimental session using a TEM and by generating an interactive visual representation of what happened during an experimental session using a TEM. The data management system and the generated interactive visual representation allows a user to access underlying image data in a novel way, by making the TEM image data filterable on any one or more metadata values. The systems and methods of metadata management described herein further improve the functioning of a computer by allowing for efficient data management of the underlying image data. In particular, the systems and methods efficiently handle the underlying image data through index files or a database, where the database is the primary record of metadata. The image files may include backups of metadata particular to the image, but the database is the primary record of metadata, meaning that data is not duplicative unnecessarily. A user can perform post-experimental filtering, sorting, and searching of the underlying image data using the metadata, which allows the image data to be analyzed without duplication of the image data and without manual review of each individual image.

As used herein, the term "filters" refers to key criteria, or metadata properties, by which an image or set of images can be identified. The key criteria or metadata properties may be measurements, settings, or calculated values, and they may come from the microscope, detectors, cameras, auxiliary equipment, or any combination thereof.

As used herein, the term "session" refers to the duration for a single microscope instance without exchanging samples or holders.

As used herein, the term "tag" refers to a name or identifier that can be attached to any number of images.

As used herein, the term "collection" refers to a set of images and their associated metadata persisted in a single database.

As used herein, the term "project" refers to a collection of sessions, even from different TEMs, into which a user can organize experimental data.

As used herein, the term "publish" refers to saving images or metadata out of the database into industry-standard formats, such as, for example, PNG files, CSV files, MP4 files, or the like.

As used herein, the term "working set" refers to the active set of images and metadata as defined by user-selected parameters, such as collections and filters.

As used herein, the term "workspace" refers to a configuration that includes specific filters, collections, and other settings. An individual workspace refers to an individual desk with individual data storage (e.g., a desktop or laptop computer). A small group workspace refers to small groups or teams that manage their data locally in a shared space.

The methods and systems of metadata management described herein are embodied in the Protochips AXON Studio, which is a metadata and image management system for reviewing TEM sessions generated through the Protochips AXON Synchronicity software package. The system and methods described herein may be implemented as part of a software environment that is connected to a TEM. The software environment may be implemented on an individual workspace, a small group workspace, or a networked workspace configured as part of a cloud-based system. The workspaces may be any type of computing device, including, for example, a desktop computer, a laptop computer, a mobile device such as a tablet or a smartphone, and/or a client in a client-server system.

The metadata management system described herein is configured to interface with an electron microscope, such as a transmission electron microscope (TEM) or a scanning transmission electron microscope (STEM), among others. The use of heating, liquid cells, and/or gas in situ systems with the TEM or STEM allows the collection of images aligned with experimental metadata. The metadata includes, for example, temperature, gas, pressure, mass spectrometer, etc. Each image has associated with it a set of metadata that describes aspects of the image or the experiment at the time the image was captured. The metadata includes the results of analysis run in AXON Studio. Math and models may be applied to a "working set" or an entire "collection" using existing metadata values. Additionally, image analysis, image filters, or selected area pixel intensity statistics that may be applied to a single image may also be applied to a "working set" or an entire "collection." These calculated metadata values can be saved to the database and used like the metadata parameters saved live with the image. They may be filtered on, plotted, published, overlaid on the image, making it easy to see how these derived metadata values change over time through the image sequence.

FIG. 1 depicts one embodiment of the system of metadata management for a transmission electron microscope described herein. Referring to FIG. 1, the computing device 100 may include at least one processor 102, at least one graphical processing unit ("GPU") 104, a memory 106, a user interface ("UI") 108, a display 110, and a network interface 112. The memory 106 may be partially integrated with the processor(s) 102 and/or the GPU(s) 104. The UI 108 may include a keyboard and a mouse. The display 110 and the UI 108 may provide any of the GUIs in the embodiments of this disclosure. AXON Studio 114 runs on the computing device 100. As noted above, the computing device 100 may be a single computing device (e.g., a laptop, a desktop computer, or a server), multiple networked computing devices, and/or a cloud server. AXON Studio may be communicatively coupled to transmission electron microscope (TEM) 116. The computing device 100 receives data from TEM 116 during one or more experimental sessions. The received data includes metadata from TEM 116.

Figure 2A:
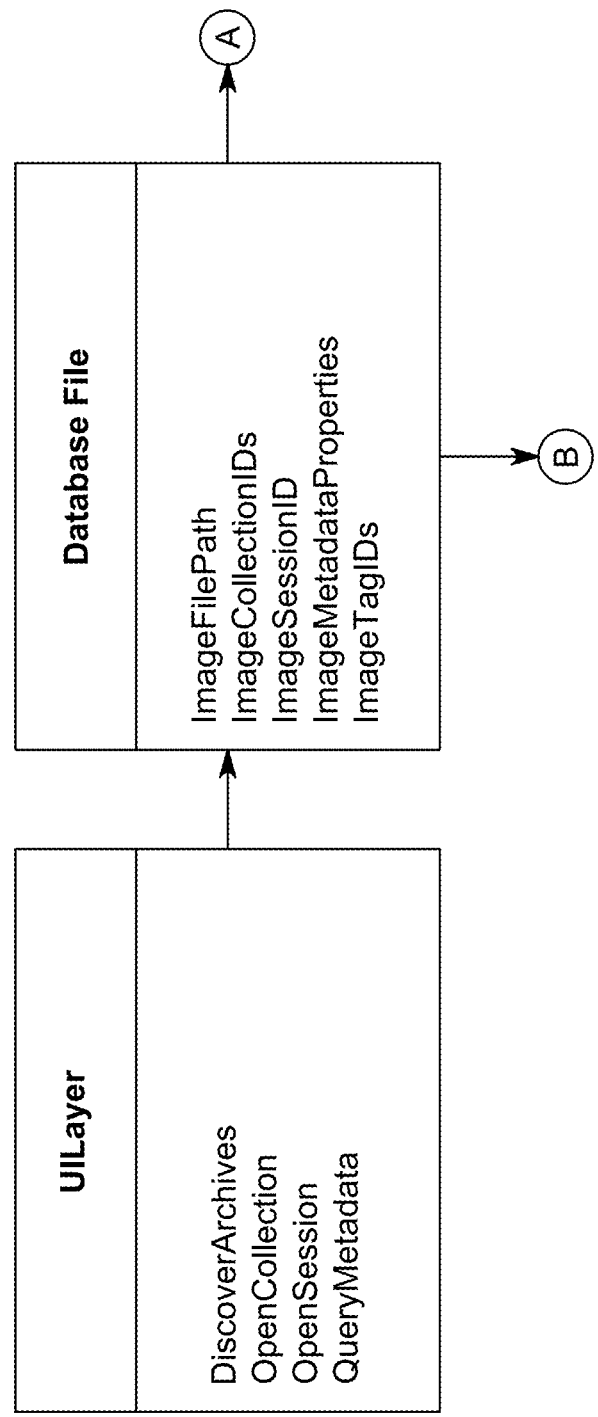
FIGS. 2A-2C depict a data architecture of an exemplary embodiment of the methods and systems of metadata management described herein.
Figure 2B:
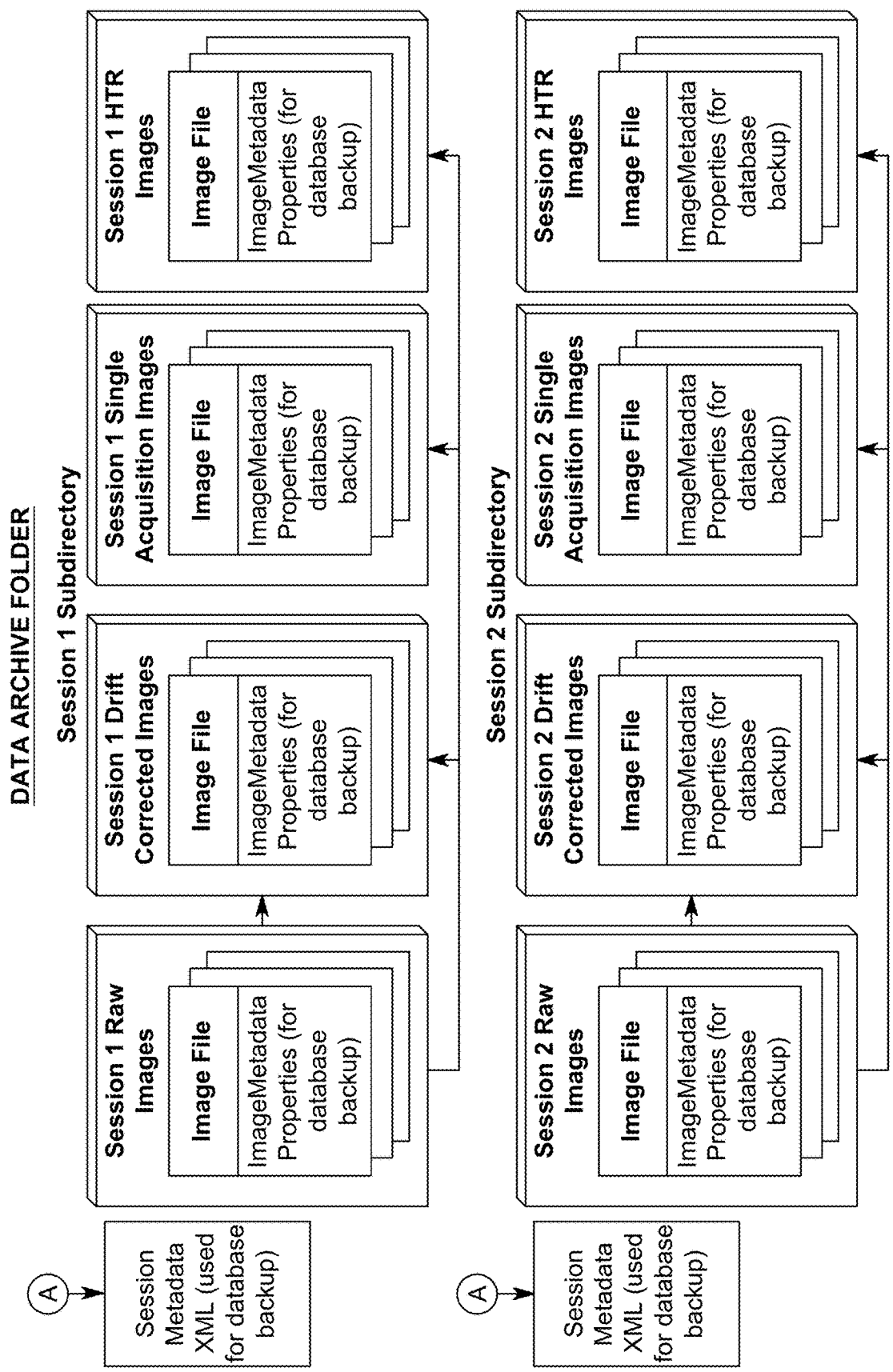
Figure 2C:
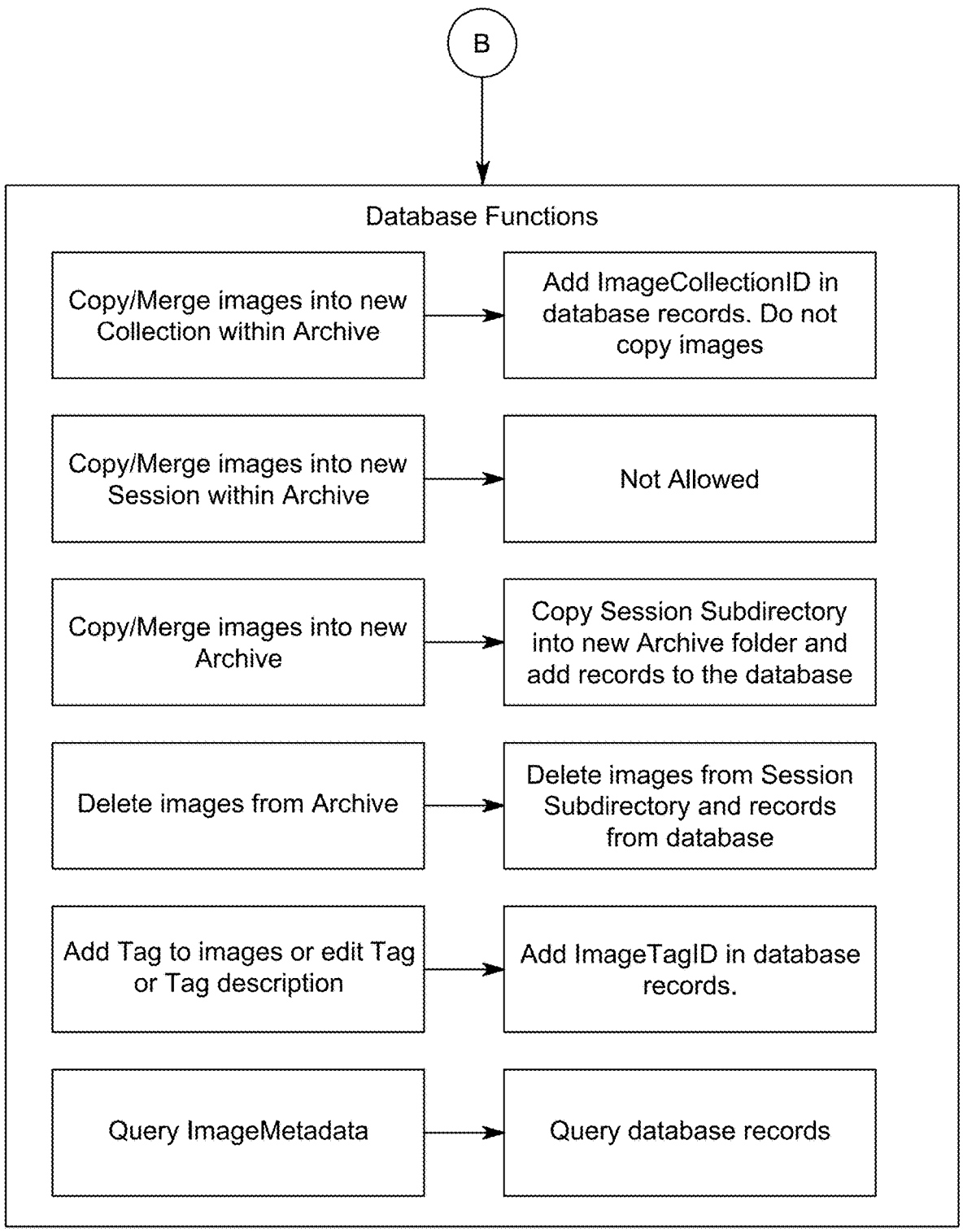

FIGS. 2A-2C depict a data architecture of an exemplary embodiment of the methods and systems of metadata management described herein. Referring to FIG. 2A, the data architecture includes a UILayer and a Database File. The Database File is communicatively coupled to one or more Data Archive Folders, as indicated by Arrow A in FIG. 2A. FIG. 2B depicts an exemplary data structure of each of the one or more Data Archive Folders. As shown in FIG. 2B, each Data Archive Folder may include one or more Session Subdirectories. The Database File includes Database Functions, as indicated by Arrow B in FIG. 2A. FIG. 2C depicts the Database Functions.

In the methods and systems of metadata management described herein, the software environment includes or is communicatively coupled to a database that stores image metadata. The database is the primary record of data, and the image metadata is used as a backup. In this way, the image metadata is used as reference data that allows for fast real-time analysis because the metadata data set is small compared to the image data set. The metadata data set is linked or associated with the image data. This allows queries of the database to be accomplished quickly to limit or highlight a particular image set. For example, a data set of 20 million records may be filtered down to only a few relevant files in less than a second by querying the relevant image metadata rather than opening and shutting each file to search through traditional image metadata.

As shown in FIG. 2B, the metadata management system comprises archives (e.g. "Data Archive Folder"), which are also referred to as Libraries, that hold session data (e.g., "Session 1 Subdirectory," "Session 2 Subdirectory," and "Session 3 Subdirectory"). Each archive is stored at a filepath or directory. Each archive may be located locally on a computer or remotely in a networked configuration, such as in a cloud-based architecture. Each archive (e.g., database folder) comprises a single database (xx.axon file) and one or many session folders. Each session folder comprises subdirectories for all image types (e.g., raw images, drift corrected images, single acquisition images, etc.), as well as session metadata that applies to the entire session (e.g., "Session Metadata"). Images are saved in the session folder using unique names for each image. The stored images include all live metadata properties saved to the PNG file as a backup, which may be used to recreate the database file if necessary.

Each image is stored in a directory (either locally or remotely), and the database references the stored images using a filepath. The database is used as the primary record of all metadata properties and may be queried to display data to the user. Although it is possible to store all images in the database, it is preferable to store the images at a filepath in a directory, as described herein, because it provides for quick querying of the database.

As shown in FIG. 2C, the database provides functions that may be applied to the images and/or sessions.

The methods and systems of metadata management described herein create an electronic lab notebook for recording, reviewing, and analyzing experimental data. Features and functionalities of the methods and systems of metadata management described herein are further explained below in the context of examples shown in the Figures.

When a TEM or STEM experiment is performed, there are a number of different types metadata that may be tracked on a per-image basis. For example, metadata may be used to track session data. The metadata may include the name, time, duration, date, location, and type of experiment of the experimental session. The metadata may further include the type of electron microscope used for the experimental session. The metadata may further include the type of environment used for the experimental session. The environment may include in-situ stimuli, in-situ environment, sample support, sample dilution, and the like. The metadata may further include a type of camera or STEM detector used for the experimental session, as well as the camera or STEM detector settings, such as image binning, resolution, brightness, contrast, and the like. The metadata may further include the time during the experimental session when a particular image was captured.

The metadata may further include measurements taken during the experimental session. The measurements may be taken at the sample or sample environment, or they may be taken either upstream or downstream from the sample or sample environment. For example, a residual gas analyzer may be used downstream of the sample to determine any by-product of a reaction. The metadata may include a mass spectrometry value of the sample, which may be taken at the sample or either upstream or downstream from the sample.

The metadata may further include a type of the sample, as well as notes relating to the sample preparation, such as sample dilution, FIB parameters, blotting parameters, sample preparation strategy, plasma cleaning parameters, surface preparation strategy, and the like. The metadata may further include flow-rate, temperature, gas composition, and pressure of the sample. The metadata may further include a focus score, which is a value that may be calculated for each image that indicates the quality of the image (e.g., by using a variance, or by using a gradient). The metadata may further include additional information, such as tags, live notes, and/or image descriptions that may be added to one or more images in a sequence or collection. The metadata value may further include particle size, particle distribution, and crystallinity percentage for one or more images in a sequence or collection.

Table 1, below, shows a non-exhaustive list of live metadata that is unique to each image.

TABLE 1

| Metadata Property | Overlay Title: | Base Units: | Applies to All Images |
|---|---|---|---|
| AXON: | | | |
| AXONDateTime | — | date/time | Yes |
| ImageNumber | — | | Yes |
| ScaleBar | — | mm/um/nm | Yes |
| MicroscopeDateTime | — | date/time | Yes |
| Tags | | | Yes |
| SessionImageNumber | | | Yes |
| AcquisitionImageNumber | | | Yes |
| DRIFT CORRECTION: | | | |
| CoordinatedDriftRate | Drift Rate: | um/ms | Only DC |
| MatchCorrelation | Match: | | Only DC |
| DriftCorrectedImageNumber | | | Only DC |
| DriftCorrectedDwell | | | Only DC |
| TotalDriftX | | um | Only DC |
| TotalDriftY | | um | Only DC |
| FOCUS ASSIST: | | | |
| FocusRoiMean | Mean Int: | | Yes |
| FocusRoiVariance | Focus Var: | | Yes |
| FocusScore | Focus S: | | Yes |
| FocusQuotient | Focus Q: | | Only DC |
| FocusScoreAlgorithm | — | | Yes |
| MICROSCOPE: | | | |
| MicroscopeName | — | | Yes |
| MicroscopeType | — | | Yes |

TABLE 1-continued

| Metadata Property | Overlay Title: | Base Units: | Applies to All Images |
|---|---|---|---|
| Acceleration Voltage | — | | Yes |
| CameraLength | — | | Yes |
| Intensity | — | | Yes |
| SpotSize | — | | Yes |
| MicroscopeImagingMode | — | | Yes |
| ConvergenceAngle | Conv: | radians | Yes |
| STEMRotation | Rotation: | deg | Yes |
| Magnification | Mag: | | Yes |
| IMAGE: | | | |
| ImagerName | — | | Yes |
| ImagerDateTime | — | | Yes |
| ImageImagePhysicalSizeX | Size X: | um | Yes |
| ImageImagePhysicalSizeY | Size Y: | um | Yes |
| ImageImagePixelsX | Size X: | | Yes |
| ImageImagePixelsY | Size Y: | | Yes |
| PixelResolutionX | — | | Yes |
| PixelResolutionY | — | | Yes |
| ImageBinning | Binning: | | Yes |
| ImageAcquisition Time | — | ms | Yes |
| ImageContrast | Contrast: | | Yes |
| ImageBrightness | Brightness: | | Yes |
| ProcessingBrightness | — | | Yes |
| ProcessingContrast | — | | Yes |
| NormalizationMode | — | | Yes |
| POSITION: | | | |
| CoordinatedPositionX | X: | um | Only DC |
| CoordinatedPositionY | Y: | um | Only DC |
| CoordinatedPositionZ | Z: | um | Only DC |
| CoordinatedPositionA | Alpha: | deg | Only DC |
| CoordinatedPositionB | Beta: | deg | Only DC |
| StageX | Stage X: | um | Yes |
| StageY | Stage Y: | um | Yes |
| StageZ | Stage Z: | um | Yes |
| StageA | Alpha: | deg | Yes |
| StageB | Beta: | deg | Yes |
| BeamX | Beam X: | um | Yes |
| BeamY | Beam Y: | um | Yes |
| BeamZ | Defocus: | um | Yes |
| BeamA | Beam Alpha: | deg | Yes |
| BeamB | Beam Beta: | deg | Yes |
| PixelShiftX | Px Shift X: | um | Only DC |
| PixelShiftY | Px Shift Y: | um | Only DC |

Live metadata may further include metadata specific to a particular in situ system that controls the sample environment, such as a liquid in situ system, a heating/electrical biasing in situ system, or a gas/heating in situ system. A non-exhaustive list of live metadata that applies to the in situ system being used may include, for example, HolderTemperature, HolderPressure, HolderGas, HolderFlowRate, Tank1Pressure, Tank1Gas, Tank2Pressure, Tank2Gas, VacuumTankPressure, VacuumTankGas, HeatingCurrent, HeatingResistance, HeatingVoltage, HeatingPower, ExperimentType, ExperimentLogFile, ExperimentElapsedTime, ChannelATemperature, ChannelACurrent, ChannelAResistance, ChannelAVoltage, ChannelAPower, ChannelBCurrent, ChannelBResistance, ChannelBVoltage, and/or ChannelBPower.

In addition to the live metadata shown above in Table 1, session metadata may be applied to an entire session rather than to a specific frame. There are varying types and amounts of metadata that may be associated with a session, so session metadata may be technique driven, which allows for flexible metadata to be added depending on the specifics of the session.

Figure 3:
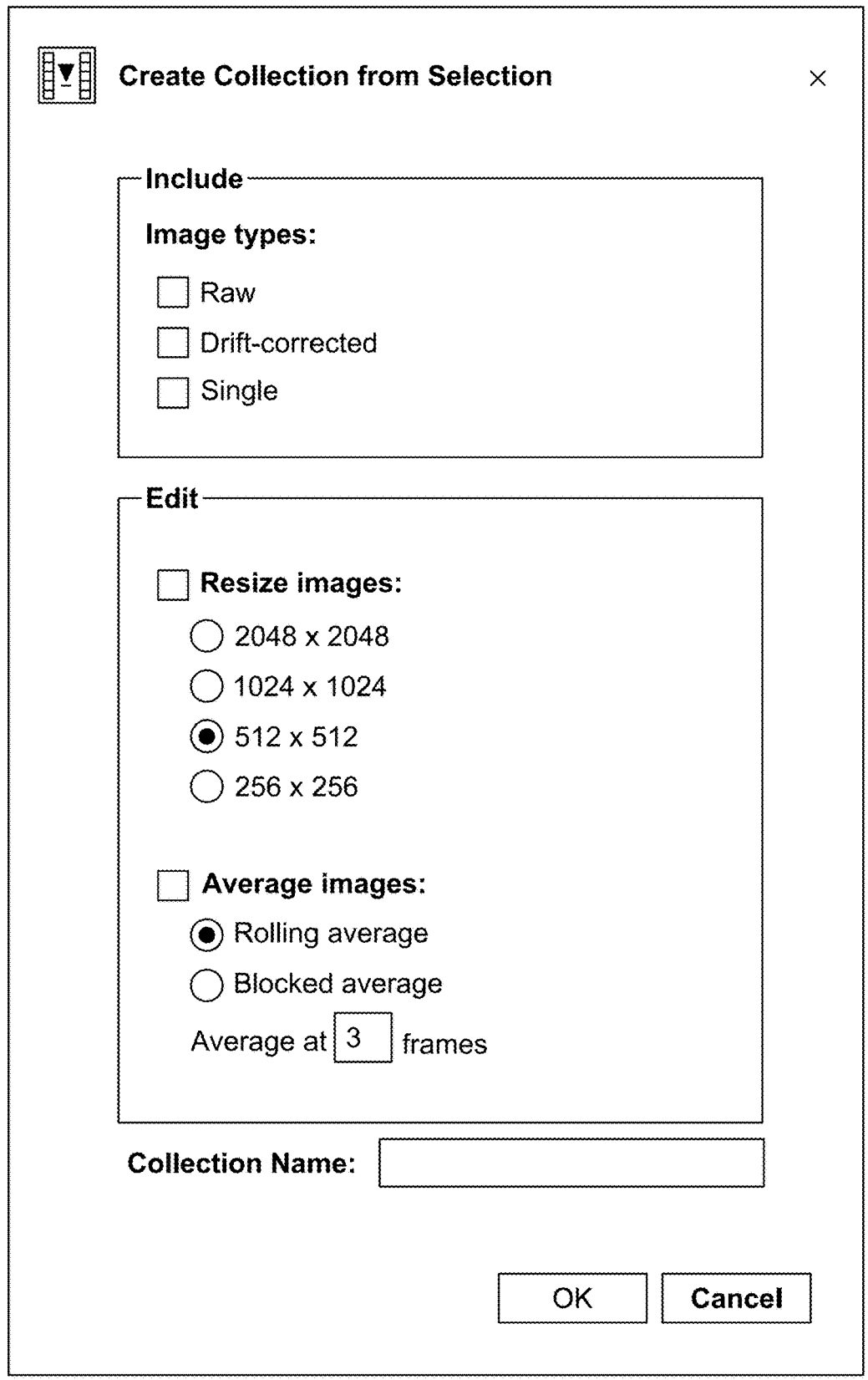
FIG. 3 depicts a user-interface screen that allows a user to create a collection of images from a filtered subset of images.

FIG. 3 depicts a user-interface screen that allows a user to create a collection of images from a filtered subset of images. The images in the selection of images may be selected by the user through filtering.

FIG. 4 depicts a user-interface screen showing an Overview Panel of the metadata management system described herein. The Overview Panel is the interface that provides the user customizable access to the underlying image data from one or more experimental sessions performed on a transmission electron microscope. As explained in the context of FIGS. 2A and 2B, the underlying image data is stored in one or more data archives, with each image being associated in the data archives with image metadata. FIG. 4 is shown as divided into three panels that are depicted in more detail in FIGS. 5, 7, and 9A-9B. The three panels of the Overview Panel are the Timeline Panel (shown in FIG. 5), the Image Panel (shown in FIG. 7), and the Image Metadata Panel (shown in FIGS. 9A-9B).

Figure 5:
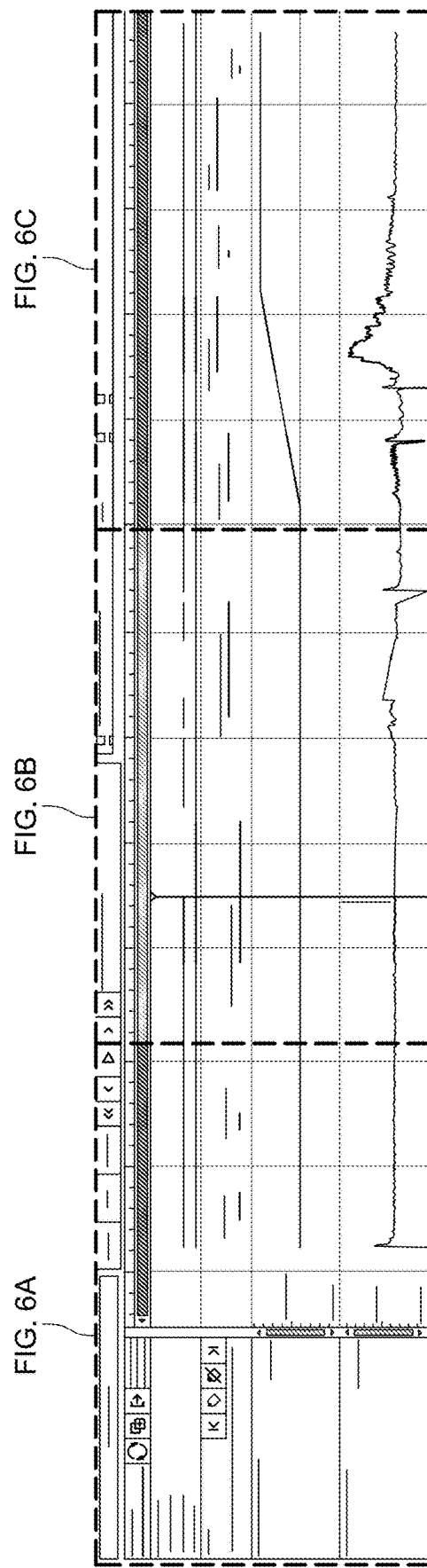
FIG. 5 depicts the Timeline Panel of the Overview Panel of the metadata management system described herein.

FIG. 5 depicts the Timeline Panel of the Overview Panel of the metadata management system described herein. FIG. 5 is shown as further divided into three panels that are depicted in more detail in FIGS. 6A-6C. The Timeline Panel provides an interactive visual map to the underlying images that are part of the metadata management system. The Timeline Panel provides an innovative interactive graphical or visual representation of correlations and/or connections between images in the underlying data of the metadata management system stored in the data archives using metadata.

The Timeline Panel provides the user with access to the image metadata of the underlying images. Then access to the image metadata allows the user to apply filters to select a subset of images from the image database. The Timeline Panel further provides an interactive visual or graphical representation that allows the user to interact with the collection of images across time. For example, the user may hover the cursor over any point on the timeline to get a preview of the particular image for that point in time in the experimental session. Additionally, the image for that point in time where the cursor is located on the timeline is displayed in the Image View Panel (shown in FIG. 7). Moving the cursor along the timeline allows the user to see how the experimental data evolves over time during the experiment.

As described, the metadata management system described herein allows for resource-efficient selecting and/or filtering of the underlying image data. The Timeline Panel further visually depicts the selected or filtered images by de-emphasizing images and/or image data that has been excluded by the filters. An example of this can be seen, for example, in FIG. 10.

The timeline further allows for plotting of any of the metadata over time as the experiment progresses. This is done by selecting the metadata in the metadata panel.

Figure 6A:
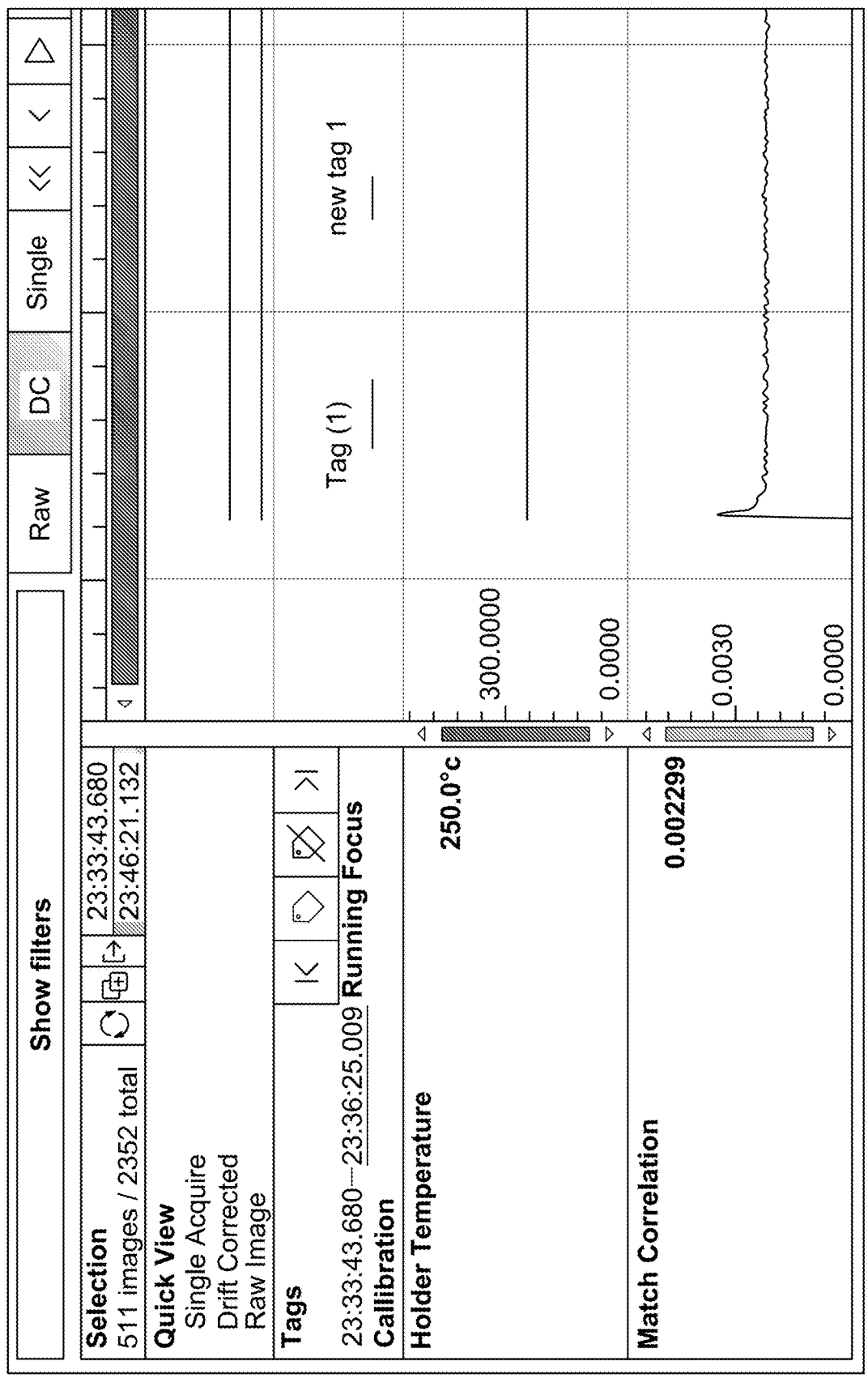
FIGS. 6A-6C each depict a detailed view of the left, middle, and right portions, respectively, of the Timeline Panel shown in FIG. 5.
Figure 6B:
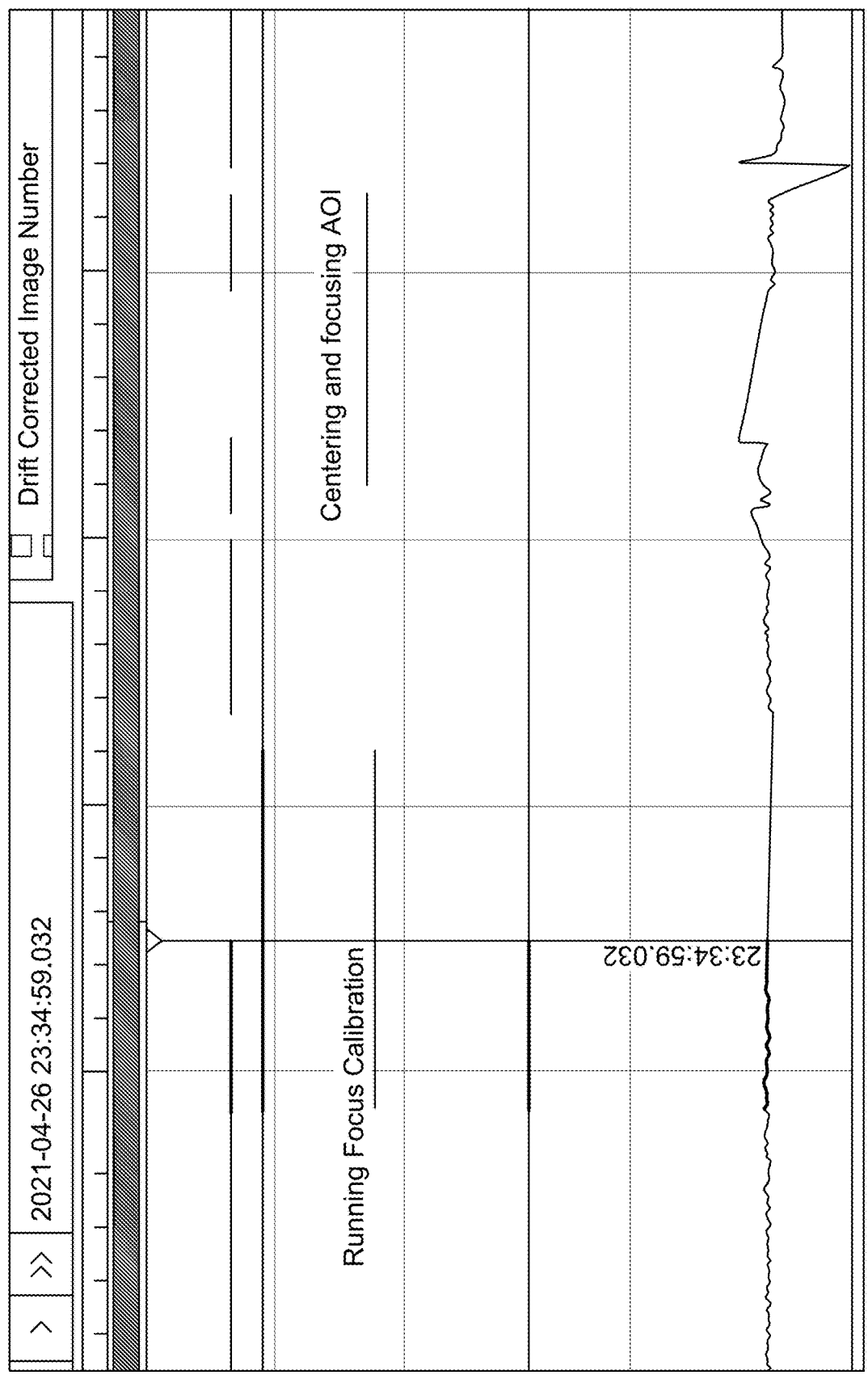
Figure 6C:
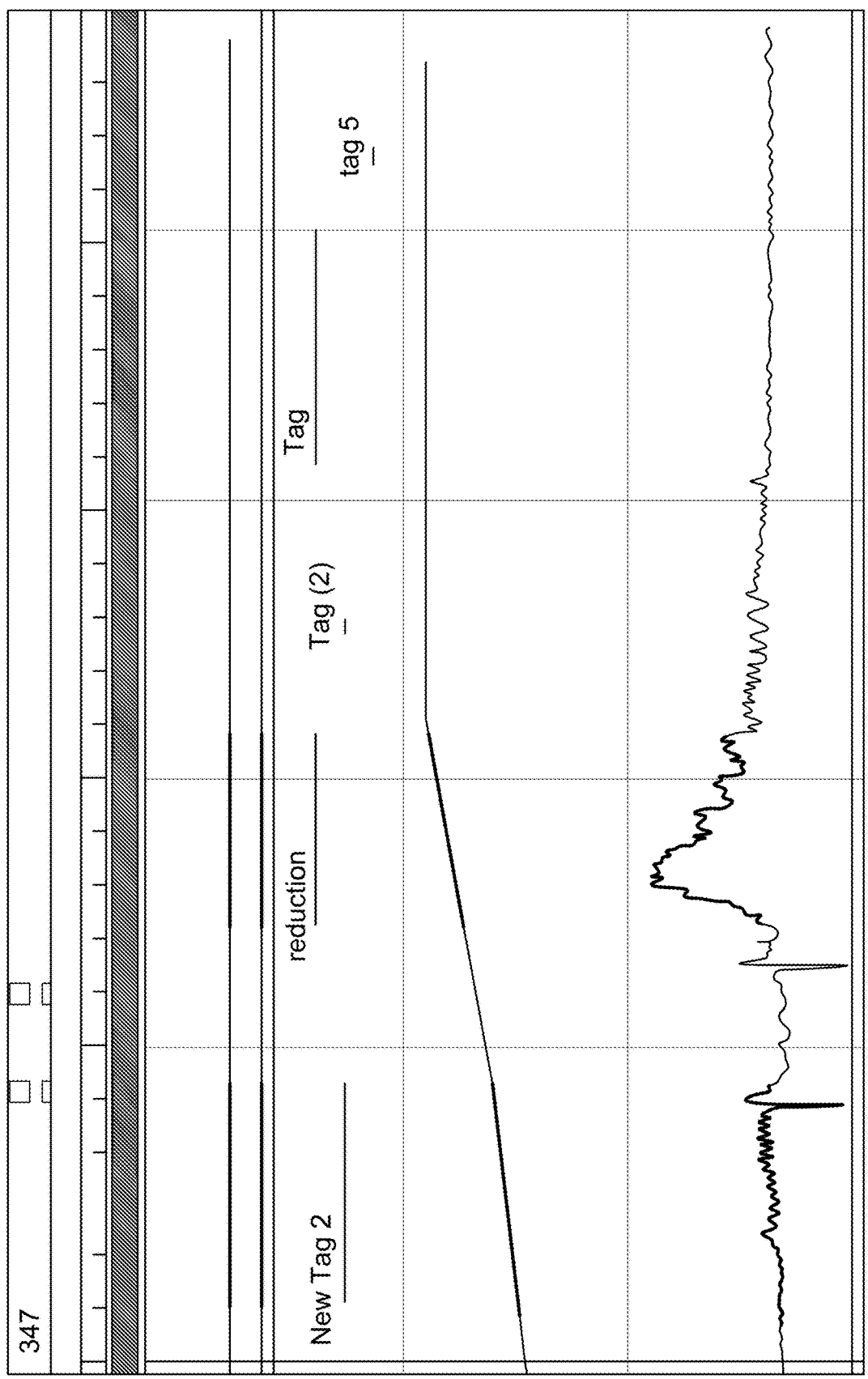

FIGS. 6A-6C each depict a detailed view of the left, middle, and right portions, respectively, of the Timeline Panel shown in FIG. 5. As can be seen from FIG. 6A, the Timeline Panel shows the metadata that is used for filtering the timeline.

Figure 7:
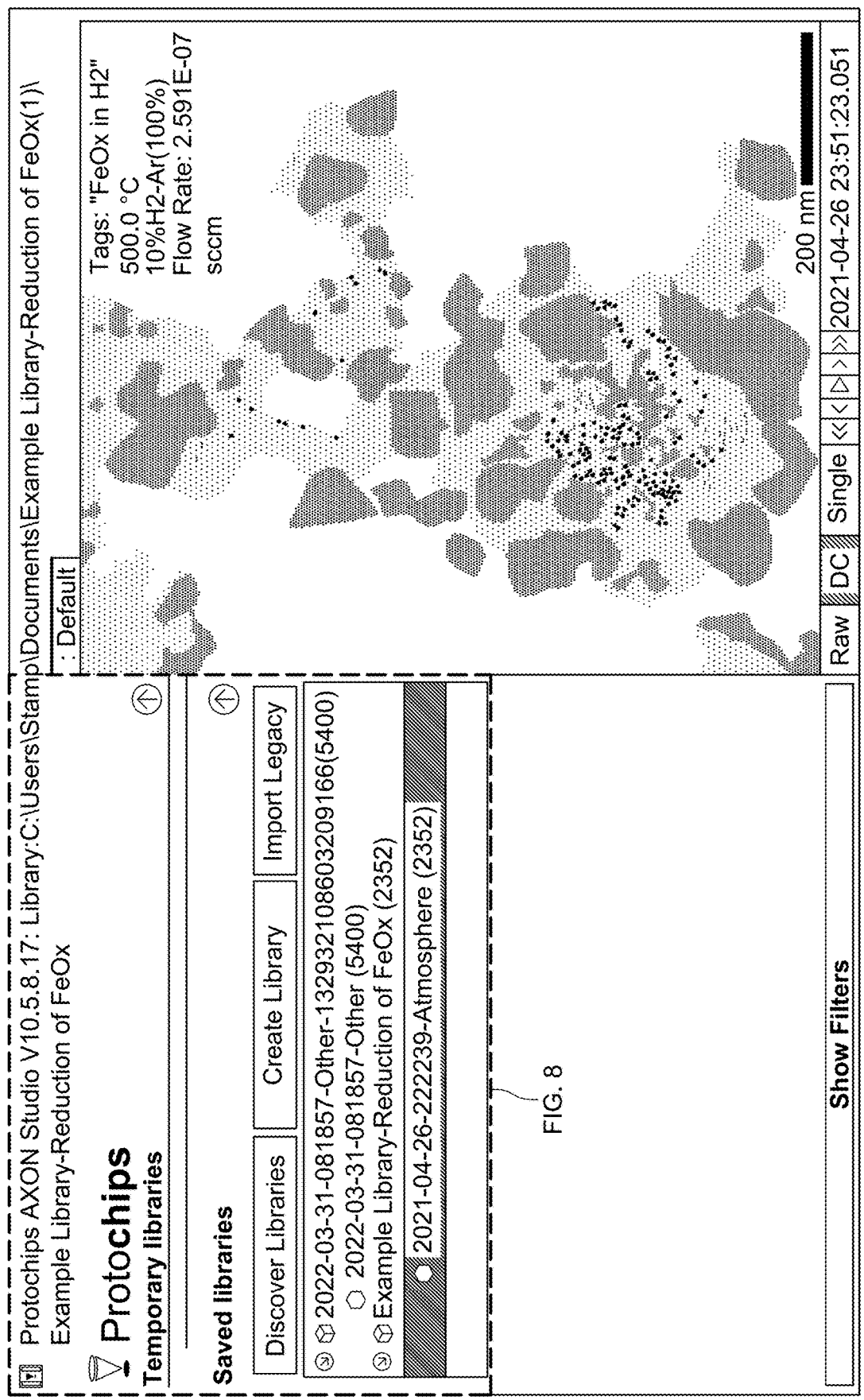
FIG. 7 depicts a detailed view of the Image Panel of the Overview Panel of the metadata management system described herein.

FIG. 7 depicts a detailed view of the Image Panel of the Overview Panel of the metadata management system described herein. FIG. 7 is shown as further indicating the Library Panel (shown in more detail in FIG. 8).

Figure 8:
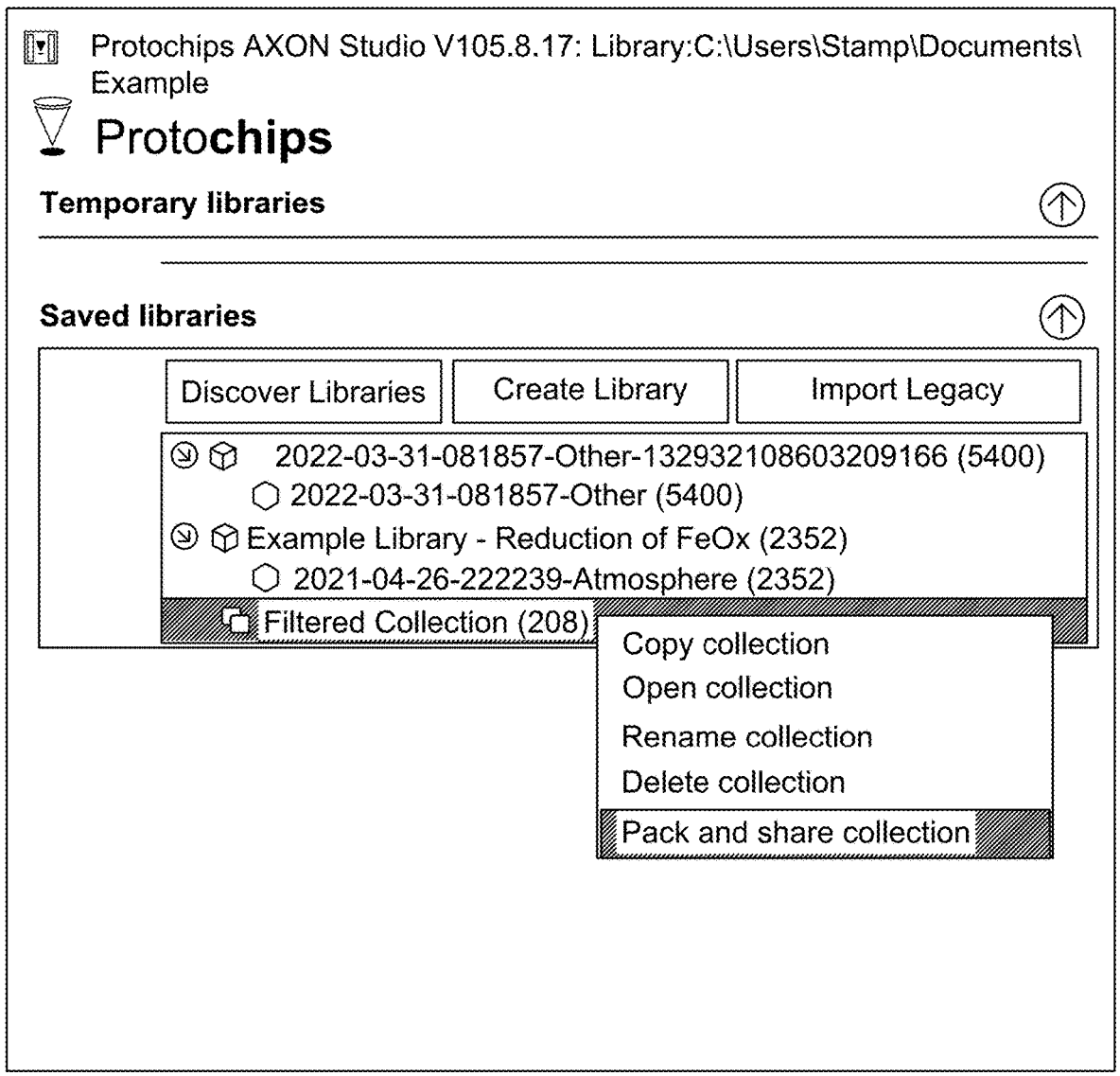
FIG. 8 depicts a detailed view of the Library Panel of the Image Panel of the Overview Panel of the metadata management system described herein.

FIG. 8 depicts a detailed view of the Library Panel of the Image Panel of the Overview Panel of the metadata management system described herein. The Library Panel provides the user interface that allows the user to create a collection of images from a filtered subset of images. The Library Panel allows the user to perform database management of the image database. Each library has one or more sessions. This is a visual representation of the data hierarchy that is maintained. The data may be further divided into collections, which may be part of a single session, or may span multiple sessions.

FIGS. 9A-9B depict a detailed view of the Image Metadata Panel of the Overview panel of the metadata management system described herein. It provides options for the user to explore the metadata of the current image that is selected by the cursor over the timeline. As the selected image on the timeline changes, the metadata displayed in the Image Metadata Panel updates in real-time to reflect the metadata for the selected image identified from the Timeline Panel.

FIG. 10 depicts a filtered view of the Overview Panel shown in FIG. 4. As explained above, the filters allow the user to filter or select a subset of images from the images in the database. FIG. 10 shows a box indicating that the Filter Panel (shown in more detail in FIG. 11). As shown in FIG. 10, when the timeline has been filtered using the Filter Panel, the timeline shows the filtered data and the data excluded by the filters. For example, sections 1002 of the timeline show excluded data that has been filtered out by the filters using metadata. Sections 1004, on the other hand, show the filtered data, meaning the data that has been selected by the filters. In one embodiment, as shown on FIG. 10, the graphical representation of the timeline shows the filtered data and the filtered portion of the timeline as emphasized (e.g., using bold and/or colors) and the excluded portion of the timeline as de-emphasized (e.g., using thin lines and/or greyed out).

Figure 11:
FIG. 11 depicts a detailed view of the Filter Panel shown in FIG. 10.

FIG. 11 depicts a detailed view of the Filter Panel shown in FIG. 10. Once a Collection or dataset has already been opened in the Overview Panel, the user may use the Filter Panel to filter out images according to any piece of captured metadata associated with the images. The filters affect the selected images shown in the Timeline Panel.

FIG. 12 depicts the Overview Panel of FIG. 4 with the FFT Analysis Panel enabled in place of the Image Metadata Panel. The FFT Analysis Panel operates with the Image View Panel. The FFT Analysis Panel is indicated on FIG. 12 as FIG. 13.

Figure 13:
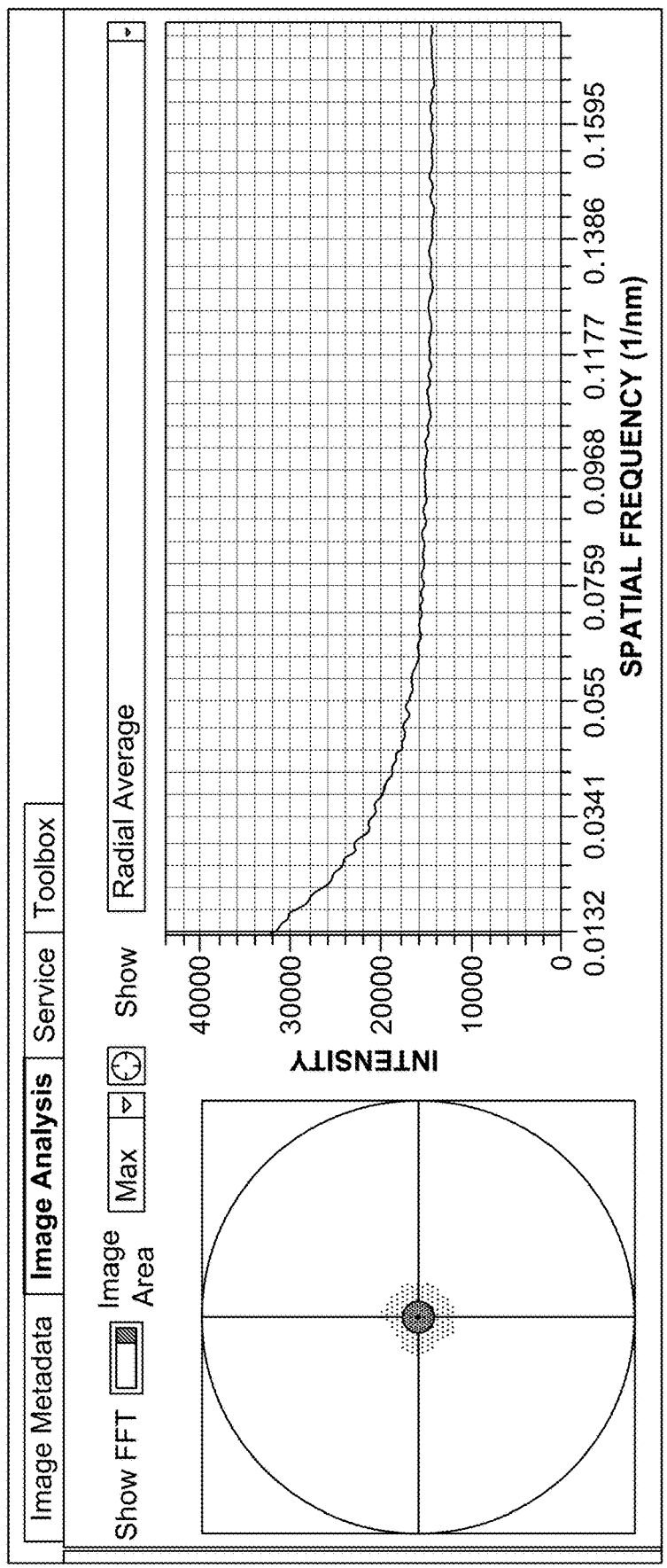
FIG. 13 depicts a detailed view of the FFT Analysis Panel for the current image that is selected by the cursor on the Timeline Panel.

FIG. 13 depicts a detailed view of the FFT Analysis Panel for the current image that is selected by the cursor on the Timeline Panel. The FFT Analysis Panel shows the radial average and spatial frequency of each image, which is calculated in real-time as the image is identified from the Timeline Panel.

Figure 14:
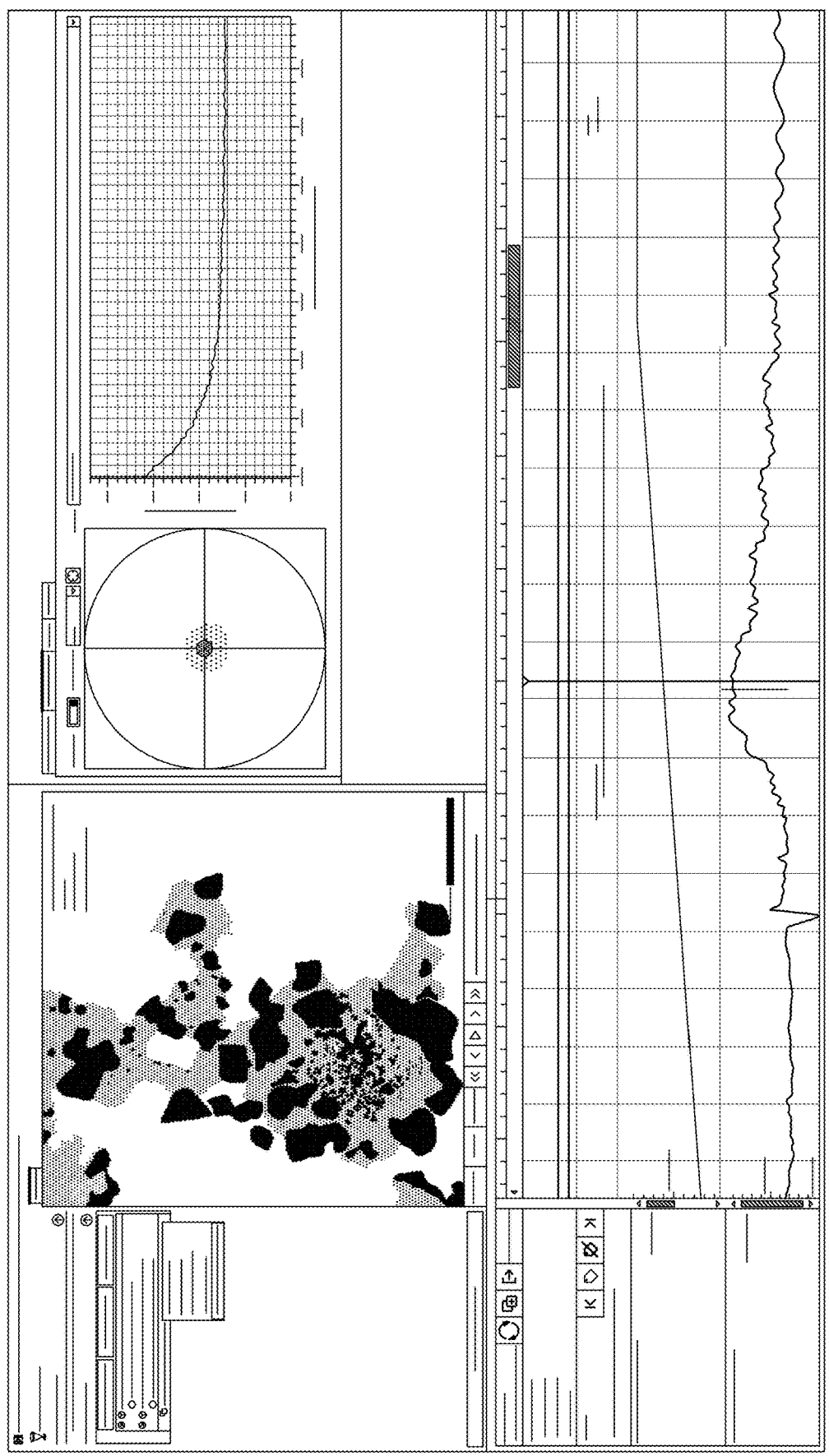
FIG. 14 depicts the Overview Panel of FIG. 12 with the Timeline Panel showing a zoomed-in view of the timeline.

FIG. 14 depicts the Overview Panel of FIG. 12 with the Timeline Panel showing a zoomed-in view of the timeline. The zoomed-in view of the timeline allows for more fine-grained control on the timeline.

Figure 15:
FIG. 15 depicts a user-interface screen for exporting the image data from the metadata management system.

FIG. 15 depicts a user-interface screen for exporting the image data from the metadata management system. The metadata management system outputs image files in one or more various industry-standard formats, so that the image data can be exported to be presented or otherwise used outside of the system.

Filtering in Context

According to embodiments of the present disclosure, metadata properties may be used to filter and/or find images, sessions, sequences, and/or collections of images. In many instances of data generated by a TEM session, filters need to be applied with context. Filters on measurements and/or calculations are best done against a chart or plot. For example, a TEM session user may plot focus score vs. time and scrub through images to quickly determine that all images with a focus score above a particular threshold are of good quality and apply a filter on the working set view only in-focus images. Such a filter may be, for example, all images where the metadata properties indicate that the focus score is above the user-defined threshold. When the user creates a collection from filtered images, for example, only the images that have not been excluded will be included in the collection.

The image analysis metadata described herein may be more valuable on a drift-corrected sequence of images because images can be normalized to show how the sample has changed over time. For example, during a TEM session, live calculations may be run on all live drift-corrected frames to generate normalized data sets. The live calculations may include focus quality, match correlation, percent crystallinity, image contrast, or the like. Drift corrected images also enable normalized focus scores against best possible or best recorded on that sample. A match correlation can be determined to isolate good frames from torn frames or bad frames. Match correlation is also useful in determining when the sample is reacting vs. when it is stable.

Additionally, other image analysis calculations may include quantifying contrast, image pixel variance, and image intensity.

The image processing calculations may be performed across the entire image or a subset of the image. The image processing calculations may be performed live as the images are captured, or they may be performed after the fact.

Metadata properties may include, for example, measurements, state and calculations from the TEM, camera, detectors and connected in-situ or auxiliary systems.

Images, sessions, sequences and/or collections of images may be filtered by in-situ stimuli or by upstream and/or downstream measurements, such as by temperature or temperature range (e.g., 500 C-600 C), gas composition, flowrate, or the like.

As another example, the images, sessions, sequences, and/or collections of images may be filtered by microscope, camera, detector or experimental state, such as by TEM vs. STEM microscope, image resolution, magnification, acceleration voltage, beam current, or the like.

As another example, the images, sessions, sequences, and/or collections of images may be filtered by calculations or characteristics, such as by particle size, particle distribution, focus quality, crystallinity percentage, composition, or the like.

As another example, the images, sessions, sequences, and/or collections of images may be filtered by session data, such as by date, type of experiment, type of sample, operator, or the like.

As another example, the images, sessions, sequences, and/or collections of images may be filtered by live notes and/or tagged image descriptions.

Timeline

According to embodiments of the present disclosure, metadata properties may be used to provide a user with an interactive graphical representation that shows a timeline of the complete history of what happened through an experiment. The complete history may be presented to the user as a timeline in the Timeline Panel that is indexed to the Image View Panel.

In one embodiment, the timeline may be passive, for example, and report status. In another embodiment, the timeline may be interactive, enabling users to select images or to provide additional functionality, such as hovering over image markers to see a preview of the image, clicking on image markers to navigate the image view to that image in the sequence, selecting images to save as a collection, selecting images to publish an image stack, providing a metadata report or video, selecting images to apply a tag, editing tag duration, text, or description, selecting images to hide or remove them from the view, selecting images to delete from a Session, Collection, or Archive, selecting images to average together into a single high-resolution image to be highlighted on the timeline, or the like. The metadata management system described herein performs averaging in a novel way by accounting for metadata when generating the average. The averaging is performed using a smart-averaging algorithm, such that only like images are included in the average. As one example, the metadata management system may only average images that were captured at the same magnification level, which is determined based on the image metadata.

For example, to reduce the total library disk size, but preserve the context needed to explain key sequences, a user may want to reduce the resolution, block average or remove every nth image from a sequences of less importance leading up to or following the key sequence. Interacting with the timeline allows users to segregate and treat sequences differently.

A user may scrub against the timeline to see how the TEM or STEM image changed. As the timeline is scrubbed, the user may reference notes and watch for metadata trends. The timeline provides to the user a context for the images.

The timeline provides a chronological lab notebook generated from live measurements and user-entered notes that is indexed to the captured images.

The timeline may include a quick-view layer that allows the user to easily visualize what image types are available. For example, a user may want to see when they were running a drift correction, or when they captured a single high-resolution capture, or when they have high temporal resolution (e.g., faster frame rate data).

The timeline may further include a tags layer. Frames or time sequences may be tagged with, for example, experimental notes or observations. The tags may be searchable, selectable, and editable.

The timeline may further include metadata plots. The metadata may be plotted against time, such that the metadata can be visualized over time. The metadata plots may be used for navigating to critical moments during the session. Peaks, valleys, and transitions in metadata plots are often sequences of interest. Users can double-click on the timeline to jump to that image.

Collections

According to embodiments of the present disclosure, metadata properties may be used to generate collections of images and their associated metadata.

A user may organize a group of images and the associated metadata into collections. A collection may span multiple sessions (i.e., time spent on the microscope from sample insertion to removing the sample at the end of the imaging session or experiment), or it may be a subset of a single session.

A single image file may be included in many different collections without being duplicated in memory. There is one underlying image file, but it can be included in the various collections using metadata tags that indicate inclusion in the collections. This avoids duplicating large files across multiple locations on a hard disk. In embodiments described herein, the original session for an image can be determined from the image, but the image may be associated with many different collections without duplicating the image data.

The collections may be nested in a hierarchical fashion (e.g., as a folder structure), but each image references back to the original session in which it was captured. Collections may include multiple sessions as a binder to organize like image sequences.

FIG. 5 depicts a user-interface screen showing creating a collection from a selection of images. The user may use metadata and/or filters to select multiple images from a session.

Collections as described herein are implemented using a database. The database is used to register a single image file into multiple collection without duplicating the image file.

Collections may be automatically created when a user "publishes" or otherwise exports an image sequence out of the database into an open format, such as a video file. This enables users to quickly reference those frames to add to or to edit.

Exemplary Use Case #1

In a first exemplary use case, consider an in situ user that wants to quickly manually identify a specific segment from an experiment by isolating a tag that the user created and then export a high-quality video by improving the signal-to-noise ratio (SNR) to clearly assess changes in atomic structure.

Using the methods and systems of metadata management described herein, the user may select a tag or sequence that represents the segment the user wants to use. The user may then filter out poorly focused frames and torn frames. The user may then perform image averaging (or image summing) to the images to improve spatial resolution in an image. This may be particularly advantageous on a drift-corrected image sequence because features are already aligned. The pixel intensities may then be averaged across a set number of frames in the image sequence to create a sequence with a preferred spatial resolution. In one embodiment, an average of 6 frames rolling may be used. In other embodiments, blocked averages may be used. When a collection of images is created with a rolling average or a blocked average, only like images may be used in the transformation. The averages will not span magnification changes, resolution changes, spot-size changes, acquisition setting changes, etc. In one embodiment, the methods and systems of metadata management described herein may preview a small set of frames (e.g., approximately 100 frames) prior to averaging the entire stack to allow the user to test and adjust the setting prior to averaging the entire stack. Finally, the user may export the video sequence of the selected segment.

Exemplary Use Case #2

In a second exemplary use case, consider an in situ user that wants to quickly manually identify a specific section of their last experiment and export to a video after cleaning up the signal to noise. The user may not know exactly what section of their experiment they are looking for, but they know they can quickly ignore the first part of the session while they were looking for a good site and warming the sample to prevent contamination. The user is only interested in a video from their high-resolution segments, and once those segments are isolated, the user will manually adjust the start and stop points based on what the user sees happening to the sample.

Using the methods and systems of metadata management described herein, the user may open a specific session. The user may then filter to a specific temperature range, for example, all temperatures over 300 degrees Celsius. The user may then filter to only see high-magnification images, for example, all images greater than 1M× (one million times magnification). The user may then select a time sequence from the remaining images after the previous filtering has been performed. The user may then filter out poorly focused frames and torn frames. The user may then create a collection of the remaining frames and name that collection. Tags with the collection name will be added to each frame in the remaining data set such that the collection can be recalled by a user. The user may then perform image averaging (or image summing) to the images to improve spatial resolution in an image. In one embodiment, an average of 2 frames rolling may be used. The user may export the video sequence of the collection.

Exemplary Use Case #3

In a third exemplary use case, consider an in situ user that wants to locate a specific TEM session from within the past year. The user wants to find a section of data that is representative of behavior within an oxidizing environment and create a video to show an advisor.

Using the methods and systems of metadata management described herein, the user may search all sessions for a specific type of catalyst and a specific microscope. From there, the user may select the particular session of interest. The user may then filter to see all frames with O2 present (since the user is looking for an oxidizing environment). The user may then select a time sequence from the remaining images after the previous filtering has been performed. The user may then filter out poorly focused frames and torn frames. The user may then export the images to video.

Exemplary Use Case #4

In a fourth exemplary use case, consider an in situ user wants to locate all TEM sessions from within the past six months using a particular catalyst because they are questioning their last result and would like to look for past consistency in their data. In their last result, the user saw that a specific transition happened to their sample at 600 degrees Celsius, so the user wants to look at all STEM data at that temperature range for all past experiments using the same environment and create a comparison to see if the transition happened at that temperature in all instances.

Using the methods and systems of metadata management described herein, the user may search all sessions for the particular catalyst they are interested in. The use may then filter for STEM images. The user may then filter to see frames with a temperature in the range of 595 degrees Celsius to 605 degrees Celsius. The user may then filter to see frames at 500k magnification. The user may then label all the remaining frames with the temperature and the date and save them as a collection.

Exemplary Use Case #5

In a fifth exemplary use case, consider an in situ user in a large lab that regularly takes data from a variety of TEMs. The user wants to search through historical session data regardless of what TEM the environmental chip was used on to locate important data.

Using the methods and systems of metadata management described herein, the user may search all sessions, regardless of microscope, for a particular core shell particle. The user may then filter to images taken at 500 degrees Celsius. The user may then manually select the session that has the best image or images taken at 500 degrees Celsius. The user may then manually select the sequence taken between 400 degrees Celsius and 550 degrees Celsius. The user may then filter out all out-of-focus images. The user may then save the remaining images as a collection. The user may then perform image averaging (or image summing) to the images to improve spatial resolution in an image. In one embodiment, an average of 3 frames rolling may be used. The user may then export the images in the collection to video.

In one embodiment, a system for generating a visual representation of experimental data from an experimental session on a transmission electron microscope using metadata from the experimental session is disclosed. The system includes a transmission electron microscope and a computer system communicatively coupled to the transmission electron microscope. The computer system includes a memory, a database, and at least one processor. The processor is configured for receiving, from the transmission electron microscope, a set of image data comprising a plurality of images captured during the experimental session performed using the transmission electron microscope. The processor is further configured for storing, in a directory in the memory, the set of image data received from the transmission electron microscope. The processor is further configured for storing, in the database, metadata associated with the image data. Metadata for a specific image includes a filepath reference to the specific image in the directory and is associated in the database with the specific image such that metadata has an associated image. The processor is further configured for filtering the metadata stored in the database to identify a subset of image data from the set of image data. The processor is further configured for generating a visual representation of the subset of image data identified using the filtered metadata in an interactive timeline format.

In various embodiments, the processor is further configured for displaying, on a graphical user interface, the returned subset of image data arranged in a timeline format.

In various embodiments, the processor is further configured for creating a collection containing the returned subset of image data. The image data is not duplicated to create the collection such that a single image may be associated with a plurality of collections.

In various embodiments, the processor is further configured for publishing the returned subset of image data. The publishing the returned subset of image data may include generating a video showing the returned subset of image data.

In one embodiment, a method for using metadata from an experimental session to perform post-experimental analysis is disclosed. The method includes storing, in a directory, a set of image data comprising a plurality of images captured during the experimental session. In one embodiment, the set of image data may include drift-corrected images. The experimental session is performed using electron microscopy. The method further includes storing, in the database, metadata associated with the image data. Metadata for a specific image includes a filepath reference to the specific image in the directory and is associated in the database with the specific image such that metadata has an associated image. The method further includes filtering the metadata stored in the database to identify a subset of image data from the set of image data. The method further includes returning the subset of image data identified using the filtered metadata.

In various embodiments, the method further includes displaying, on a graphical user interface, the returned subset of image data arranged in a timeline format.

In various embodiments, the method further includes creating a collection containing the returned subset of image data. The image data is not duplicated to create the collection such that a single image may be associated with a plurality of collections.

In various embodiments, the method further includes publishing the returned subset of image data. The publishing the returned subset of image data may include generating a video showing the returned subset of image data.

In another embodiment, a computer system for performing post-experimental analysis using metadata from an experimental session is disclosed. The computer system includes a memory, a database, and at least one processor. The processor is configured for storing, in a directory in the memory, a set of image data comprising a plurality of images captured during the experimental session. The experimental session is performed using electron microscopy. In one embodiment, the set of image data includes drift-corrected images. The processor is further configured for storing, in the database, metadata associated with the image data. Metadata for a specific image includes a filepath reference to the specific image in the directory and is associated in the database with the specific image such that metadata has an associated image. The processor is further configured for filtering the metadata stored in the database to identify a subset of image data from the set of image data. The processor is further configured for returning the subset of image data identified using the filtered metadata.

In various embodiments, the processor is further configured for displaying, on a graphical user interface, the returned subset of image data arranged in a timeline format.

In various embodiments, the processor is further configured for creating a collection containing the returned subset of image data. The image data is not duplicated to create the collection such that a single image may be associated with a plurality of collections.

In various embodiments, the processor is further configured for publishing the returned subset of image data. The returned subset of image data includes generating a video showing the returned subset of image data.

In another embodiment, a non-transitory computer-readable storage medium storing instructions to be implemented on at least one computing device including at least one processor is disclosed. The instructions when executed by the at least one processor cause the at least one computing device to perform a method of using metadata from an experimental session to perform post-experimental analysis. The method includes storing, in a directory, a set of image data comprising a plurality of images captured during the experimental session. The experimental session is performed using electron microscopy. In one embodiment, the set of image data includes drift-corrected images. The method further includes storing, in the database, metadata associated with the image data. Metadata for a specific image includes a filepath reference to the specific image in the directory and is associated in the database with the specific image such that metadata has an associated image. The method further includes filtering the metadata stored in the database to identify a subset of image data from the set of image data. The method further includes returning the subset of image data identified using the filtered metadata.

In various embodiments, the instructions further cause the at least one computing device to display, on a graphical user interface, the returned subset of image data arranged in a timeline format.

In various embodiments, the instructions further cause the at least one computing device to create a collection containing the returned subset of image data. Image data is not duplicated to create the collection such that a single image may be associated with a plurality of collections.

In various embodiments, the instructions further cause the at least one computing device to publish the returned subset of image data. Publishing the returned subset of image data may include generating a video showing the returned subset of image data.

In the various embodiments described above, the metadata may include any one or more of the following: a value identifying the experimental session, a value indicating a type of electron microscope used for the experimental session, a value indicating a type of environment used for the experimental session, a value indicating a type of camera or STEM detector used for the experimental session, values indicating camera or STEM detector settings used for the experimental session, a measurement of the sample taken during the experimental session, a flow-rate of the sample during the experimental session, a date of the experimental session, a value indicating a type of experiment of the experimental session, a value indicating a type of sample of the experimental session, values indicating sample preparation notes of the sample of the experimental session, a focus score value that indicates quality of the associated image, a temperature value of the sample when the associated image was captured, a gas composition in the sample when the associated image was captured, a pressure value of the sample when the associated image was captured, a mass spectrometry value of the sample when the associated image was captured, a time value indicating when during the experiment the associated image was captured, a tag for the associated image, a live note for the associated image, an image description for the associated image data, a value indicating particle size for the associated image, a value indicating particle distribution for the associated image, a value indicating crystallinity percentage for the associated image. The measurement of the sample taken during the experimental session is an upstream measurement or a downstream measurement. The mass spectrometry value of the sample is an upstream value or a downstream value. As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter situation scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described above with reference to flowchart illustrations and/or block diagrams of methods, apparatus (systems) and computer program products according to embodiments of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the present disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the present disclosure in the form disclosed. Many modifications and variations will be apparent to those of ordinary skill in the art without departing from the scope and spirit of the present disclosure. The embodiments were chosen and described in order to best explain the principles of the present disclosure and the practical application, and to enable others of ordinary skill in the art to understand the present disclosure for various embodiments with various modifications as are suited to the particular use contemplated.

These and other changes can be made to the disclosure in light of the Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

What is claimed is:

1. A system for managing metadata from an experimental session on an electron microscope, the system comprising:
    an electron microscope; and
    a computer system communicatively coupled to the electron microscope, the computer system comprising:
        a memory;
        a database; and
        at least one processor configured for:
            receiving, from the electron microscope, metadata associated with the experimental session performed using the electron microscope;
            receiving, from the electron microscope, image data comprising a plurality of images captured during the experimental session;
            storing the metadata;
            storing the image data;
            associating at least some of the metadata with one or more images of the plurality of images in the image data;
            filtering the image data based on the associated metadata; and
            generating a visual representation of the filtered image data.

2. The system of claim 1, wherein the at least one processor is further configured for generating additional metadata based on the image data or the metadata received from the electron microscope.

3. The system of claim 2, wherein the additional metadata is generated by performing image processing of at least some of the image data, wherein the image processing is performed as the image data is captured by the electron microscope or as part of post-processing after the image data has been captured by the electron microscope.

4. The system of claim 1, wherein the metadata includes session data associated with the experimental session rather than a specific image from the plurality of images.

5. The system of claim 1, wherein the metadata includes measurements taken during the experimental session.

6. The system of claim 1, wherein the metadata includes a note input by a user related to the image data or the experimental session.

7. The system of claim 1, wherein the metadata includes a determined focus score associated with a specific image from the plurality of images.

8. The system of claim 1, wherein the metadata is received separately from the image data.

9. The system of claim 1, wherein metadata associated with a specific image from the plurality of images is received separately from a specific image the metadata is associated with.

10. A computer system for managing metadata from an experimental session on an electron microscope, the computer system comprising:
    a memory;
    a database; and
    at least one processor configured for:
        receiving, from the electron microscope, metadata associated with the experimental session performed using the electron microscope;
        receiving, from the electron microscope, image data comprising a plurality of images captured during the experimental session;
        storing the metadata;
        storing the image data;
        associating at least some of the metadata with one or more images of the plurality of images in the image data;
        generating a visual representation of at least one image of the plurality of images in the image data,
            wherein the visual representation includes an interactive timeline, the at least one image of the plurality of images, and metadata associated with the at least one image of the plurality of images; and
        updating the visual representation of the at least one image of the plurality of images and the associated metadata for the interactive timeline.

11. The computer system of claim 10, wherein the at least one processor is further configured for generating additional metadata based on the image data or the metadata received from the electron microscope.

12. The computer system of claim 11, wherein the additional metadata is generated by performing image processing of at least some of the image data, wherein the image processing is performed as the image data is captured by the electron microscope or as part of post-processing after the image data has been captured by the electron microscope.

13. The computer system of claim 10, wherein the metadata includes session data associated with the experimental session rather than a specific image from the plurality of images.

14. The computer system of claim 10, wherein the metadata includes measurements taken during the experimental session.

15. The computer system of claim 10, wherein the metadata includes a note input by a user related to the image data or the experimental session.

16. The computer system of claim 10, wherein the metadata includes a determined focus score associated with a specific image from the plurality of images.

17. The computer system of claim 10, wherein the metadata is received separately from the image data.

18. The computer system of claim 10, wherein metadata associated with a specific image from the plurality of images is received separately from a specific image the metadata is associated with.

19. A non-transitory computer-readable storage medium, the non-transitory computer-readable storage medium storing instructions to be implemented on at least one computing device including at least one processor, the instructions when executed by the at least one processor cause the at least one computing device to perform a method of managing metadata from an experimental session on an electron microscope, the method comprising:
  receiving, from the electron microscope, metadata associated with the experimental session performed using the electron microscope;
  receiving, from the electron microscope, image data comprising a plurality of images captured during the experimental session;
  storing the metadata;
  storing the image data;
  associating at least some of the received metadata with one or more images of the plurality of images in the image data;
  filtering the image data based on the metadata;
  generating a collection of filtered image data; and
  associating at least one metadata tag with the collection of filtered image data.

20. The non-transitory computer-readable storage medium of claim 19, wherein the instructions further cause the at least one computing device to generate additional metadata based on the image data or the metadata received from the electron microscope.

* * * * *